(12) United States Patent
Forbes

(10) Patent No.: US 10,896,431 B2
(45) Date of Patent: *Jan. 19, 2021

(54) METHODS AND SYSTEMS FOR ASSESSING PSYCHOLOGICAL CHARACTERISTICS

(71) Applicant: Forbes Consulting Group, LLC, Lexington, MA (US)

(72) Inventor: David Lowry Forbes, Lincoln, MA (US)

(73) Assignee: Forbes Consulting Group, LLC, Needham, MA (US)

( * ) Notice: Subject to any disclaimer, the term of this patent is extended or adjusted under 35 U.S.C. 154(b) by 806 days.

This patent is subject to a terminal disclaimer.

(21) Appl. No.: 15/419,755

(22) Filed: Jan. 30, 2017

(65) Prior Publication Data

US 2017/0300930 A1    Oct. 19, 2017

Related U.S. Application Data

(63) Continuation of application No. 12/872,531, filed on Aug. 31, 2010, now Pat. No. 9,558,499, which is a (Continued)

(51) Int. Cl.
*G06Q 30/02* (2012.01)
*A61B 5/16* (2006.01)
(Continued)

(52) U.S. Cl.
CPC ......... *G06Q 30/02* (2013.01); *A61B 5/04842* (2013.01); *A61B 5/16* (2013.01);
(Continued)

(58) Field of Classification Search
CPC ........ G16H 10/20; G16H 50/70; A61B 5/165; G06F 16/436

See application file for complete search history.

(56) References Cited

U.S. PATENT DOCUMENTS 6,292,688 B1    9/2001  Patton
6,826,540 B1    11/2004 Plantec et al.
(Continued)

FOREIGN PATENT DOCUMENTS

CN    1516561    7/2004
CN    1739451    3/2006
(Continued)

OTHER PUBLICATIONS

Australian Examination Report issued in Australian application 2017201444 dated Jun. 2, 2017 (4 pages).
(Continued)

*Primary Examiner* — Nathan Hillery
(74) *Attorney, Agent, or Firm* — Fish & Richardson P.C.

(57) ABSTRACT

A method for assessing a pre-cognitive emotional response from a test subject, using responses obtained during the first moments of brain activity after presentation of a stimulus, includes exposing the test subject to a visual stimulus for between approximately 500 milliseconds and approximately 1 second, and receiving an input from the subject while the subject is exposed to the visual stimulus or within approximately 300 milliseconds after the subject is first exposed to the stimulus. The method further includes storing, in response to receiving the input, a user response that identifies one of a plurality of emotional reactions that is associated with the visual stimulus. Each of the exposing, receiving, and storing acts is repeated for a plurality of visual stimuli. The method further includes determining, based on each of the stored user responses, one or more dominant emotional characteristics of the subject.

18 Claims, 11 Drawing Sheets

Related U.S. Application Data continuation-in-part of application No. 12/713,539, filed on Feb. 26, 2010, now Pat. No. 9,603,564.

(60) Provisional application No. 61/156,236, filed on Feb. 27, 2009.

(51) Int. Cl.

| | |
|---|---|
| *G06Q 10/06* | (2012.01) |
| *A61B 5/0484* | (2006.01) |
| *G09B 7/00* | (2006.01) |
| *G06K 9/00* | (2006.01) |
| *G06F 16/435* | (2019.01) |
| *G16H 50/70* | (2018.01) |
| *G16H 10/20* | (2018.01) |
| *G16H 50/20* | (2018.01) |

(52) U.S. Cl.
CPC ............. *A61B 5/165* (2013.01); *A61B 5/167* (2013.01); *G06F 16/436* (2019.01); *G06K 9/00308* (2013.01); *G06Q 10/06398* (2013.01); *G06Q 30/0203* (2013.01); *G06Q 30/0242* (2013.01); *G09B 7/00* (2013.01); *G16H 50/70* (2018.01); *G16H 10/20* (2018.01); *G16H 50/20* (2018.01)

(56) References Cited

U.S. PATENT DOCUMENTS

| | | | |
|---|---|---|---|
| 7,606,726 | B2 | 10/2009 | Nelson |
| 7,720,784 | B1 | 5/2010 | Froloff |
| 7,942,816 | B2 | 5/2011 | Satoh et al. |
| 9,558,499 | B2 | 1/2017 | Forbes |
| 2003/0182123 | A1 | 9/2003 | Mitsuyoshi |
| 2004/0082862 | A1 | 4/2004 | Chance |
| 2004/0210159 | A1 | 10/2004 | Kibar |
| 2005/0054904 | A1 | 3/2005 | El-Nokaly |
| 2005/0062888 | A1 | 3/2005 | Wood et al. |
| 2005/0209709 | A1 | 9/2005 | Bradshaw |
| 2006/0153531 | A1 | 7/2006 | Kanegae et al. |
| 2006/0229505 | A1 | 10/2006 | Mundt |
| 2007/0050151 | A1 | 3/2007 | Satoh et al. |
| 2007/0066916 | A1 | 3/2007 | Lemos |
| 2008/0037841 | A1 | 2/2008 | Ogawa |
| 2008/0065468 | A1 | 3/2008 | Berg et al. |
| 2008/0097235 | A1 | 4/2008 | Ofek et al. |
| 2008/0101660 | A1 | 5/2008 | Seo et al. |
| 2008/0144882 | A1 | 6/2008 | Leinbach et al. |
| 2008/0255949 | A1 | 10/2008 | Genco |
| 2009/0024049 | A1 | 1/2009 | Pradeep et al. |
| 2009/0083118 | A1 | 3/2009 | Kallery et al. |
| 2009/0062629 | A1 | 5/2009 | Pradeep et al. |
| 2009/0275006 | A1 | 11/2009 | Cvencek |
| 2009/0285456 | A1 | 11/2009 | Moon et al. |
| 2010/0009325 | A1 | 1/2010 | Afanasiev et al. |
| 2010/0010317 | A1 | 1/2010 | De Lemos |
| 2010/0055656 | A1 | 3/2010 | Sturm et al. |
| 2010/0145215 | A1 | 6/2010 | Pradeep |
| 2010/0179950 | A1 | 7/2010 | Willcock |
| 2010/0221687 | A1 | 9/2010 | Forbes |
| 2010/0266213 | A1 | 10/2010 | Hill |
| 2011/0020778 | A1 | 1/2011 | Forbes |
| 2011/0161011 | A1 | 6/2011 | Hasson |
| 2012/0035428 | A1 | 2/2012 | Roberts et al. |
| 2012/0071785 | A1 | 3/2012 | Forbes |
| 2013/0085808 | A1 | 4/2013 | Forbes |
| 2013/0185141 | A1 | 7/2013 | Pradeep |

FOREIGN PATENT DOCUMENTS

| | | |
|---|---|---|
| CN | 101815467 | 8/2010 |
| CN | 103262143 A | 8/2013 |
| EP | 2401733 | 1/2012 |
| EP | 2612312 | 7/2013 |
| IN | 1666/CHENP2013 | 11/2014 |
| JP | 2009530071 | 8/2009 |
| RU | 2166280 C2 | 5/2001 |
| RU | 2289310 C2 | 12/2006 |
| RU | 2013114331 | 10/2014 |
| RU | 2595964 C2 | 8/2016 |
| WO | WO 2007/0106083 | 9/2007 |
| WO | WO2007/106518 | 9/2007 |
| WO | WO2008/023260 | 2/2008 |
| WO | WO2010/099443 | 9/2010 |
| WO | WO2012/030652 | 3/2012 |
| WO | WO2013/055535 | 4/2013 |
| WO | WO2014/081805 | 5/2014 |

OTHER PUBLICATIONS

European Communication from European application No. 11822401.3 dated Mar. 1, 2017 (5 pages).
U.S. Appl. No. 12/872,531, filed Aug. 31, 2010, David L. Forbes.
U.S. Appl. No. 12/713,539, filed Feb. 26, 2010, David L. Forbes.
Canadian Office action issued in Canadian application 2809827 dated Jul. 12, 2017 (10 pages).
Office Action in Indian Application No. 1666/CHENP/2013, dated Oct. 15, 2019, 5 pages.
Australian office action from Australian application 2017201444 dated Dec. 21, 2017 (4 pages).
Chinese Office action with English translation from Chinese application 201180051770.3, dated Oct. 20, 2015, (19 pages).
European Communication from European Application 10746912.4 dated May 31, 2016 (6 pages).
Office Action in Australian Application No. 2015200472, dated Mar. 2, 2016, (5 pages).
Office Action in Australian Application No. 2015200496, dated Mar. 8, 2016 (3 pages).
Russian Decision on Grant for Application No. 2013114331/08(021174) Jun. 3, 2016 (16 pages).
International Search Report and Written Opinion for International Patent Application No. PCT/US2010/025588 dated May 13, 2010 (9 pages).
International Search Report for PCT/US2011/049383 dated Dec. 29, 2011 (2 pages).
International Preliminary Report on Patentability for International Patent Application No. PCT/US2010/025588 dated Aug. 30, 2011 (8 pages).
Schupp, Harald, T. et al., "The selective processing of emotional visual stimuli while detecting auditory targets: An ERP analysis", Brain Research 1230 (2008) pp. 168-176 (9 pages).
International Search Report and Written Opinion for International Patent Application No. PCT/US2013/070966 dated Feb. 4, 2014 (13 pages).
Office action from Australian Application No. 2010217803, dated May 3, 2013 (5 pages).
Office action from Canadian Application No. 2753872 dated Sep. 12, 2013 (3 pages).
Extended European Search Report for EP application No. 10746912.4 dated Sep. 11, 2013 (8 pages).
Examination report from Australian Application No. 2011296331 dated May 3, 2013 (5 pages).
International Search Report and Written Opinion from PCT application No. PCT/US2012/057943 dated Jan. 7, 2013 (14 pages).
Cunningham, William A., et al, "Attitudes to the Right- and Left: Frontal ERP Asymmetries Associated with Stimulus Valence and Processing Goals", ERP Asymmetries in Evaluation, NeuroImage, 28, pp. 827-834, 2005 (30 pages).
Cunningham, William A., et al., "Attitudes and evaluations: a social cognitive neuroscience perspective", Science Direct, www.sciencedirect.com 1364-6613/2007 Elsevier Ltd. All rights reserved. doi:10.1016/j.tics.2006.12.005, Trends in Cognitive Sciences, vol. 11, No. 3, pp. 97-104, specifically p. 102, Diagram Box 2, Feb. 7, 2007 (8 pages).
Cunningham, William A., et al., "The iterative reprocessing model: a multilevel framework for attitudes and evaluation", Social Cognition, vol. 25, No. 5, pp. 736-760, 2007 (25 pages).

(56) References Cited

OTHER PUBLICATIONS

Damasio, Antonio, "Self Comes to Mind: Constructing the Conscious Brain", Pantheon Books, Random House, Inc., copyright 2010 (592 pages).
Grill-Spector, Kalanit, et al., "Visual Recognition: As soon as you know it is there, you know what it is", Psychological Science, Research Article, American Psychological Society, vol. 16, No. 2, 2005 (9 pages).
Luo, Qian, et al., "Neural dynamics for facial threat processing as revealed by gamma band synchronization using MEG", NIH Public Access, Author Manuscript, PMC Jan. 15, 2008, published Neuroimage, Jan. 15, 2007; 34(2): 839-847 (18 pages).
Rudrauf, David, et al., "Enter feelings: Somatosensory responses following early stages of visual induction of emotion", International Journal of Psychophysiology, 72, pp. 13-23, 2009 (11 pages).
Rudrauf, David, et al., "Rapid Interactions between Venral Visual Stream and Emotion-Related Structures Rely on a Two-Pathway Architecture", the Journal of Neuroscience, Mar. 12, 2008, 28(11): pp. 2793-2803 (11 pages).
Scott, Lisa S., et al., "Electrophysiological Correlates of Facial Self-Recognition in Adults and Children", Cognition, Brain, Behavior, vol. IX(3), pp. 211-238, 2005 (28 pages).
Response to Australian Office action filed on Aug. 1, 2014 for Australian application No. 2010217803 (48 pages).
Batty, M. et al.,"Early processing of the six basic facial emotional expressions", Cognitive Brain Research, 2003, vol. 17, pp. 613-620.
Examination Report from Australian application No. 2010217803 dated Sep. 1, 2014 (7 pages).
Communication for EP application No. 10746912.4 dated Sep. 27, 2013 (1 page).
Office action from Chinese application 201180051770.3 dated Jan. 7, 2015 (11 pages).
European communication for EP application 11822401.3 dated Apr. 25, 2013 (2 pages).
Response to extended European Search Report for EP application No. 10746912.4 filed on Apr. 7, 2014 (10 pages).
Chinese Office action with English translation from Chinese application 201180051770.3 dated Jan. 7, 2015 (23 pages).
International Preliminary Report on Patentability from PCT application PCT/US2011/049383 dated Mar. 14, 2013 (9 pages).
International Preliminary Report on Patentability from PCT application PCT/US2012/057943 dated Apr. 10, 2014 (7 pages).
International Preliminary Report on Patentability from PCT application PCT/US2010/025588 dated Aug. 30, 2011 (8 pages).
International Search Report and Written Opinion from PCT application PCT/US2011/049383 dated Dec. 29, 2011 (7 pages).
Examination Report from Canadian Application 2753872 dated Mar. 12, 2015 (4 pages).
Examination Report from European Application 11822401.3 dated Apr. 17, 2015 (3 pages).
International Preliminary Report on Patentability from PCT application PCT/US2013/070966 dated Jun. 4, 2015 (7 pages).
Voluntary Amendment filed in Australian Application 2011296331 dated Mar. 12, 2013 (13 pages).
Response to Examination report dated Sep. 12, 2013 in Canadian Application 2753872, filed on Mar. 12, 2014 (24 pages).
Batty, Magali, et al., "Early processing of the six basic facial emotional expressions", Cognitive Brain Research 17, pp. 613-620, May 22, 2003 (8 pages).
European Communication from European Application 11822401.3 dated May 4, 2015 (6 pages).
Office action with English translation issued in Russian application No. 2013114331 dated Aug. 14, 2015 (12 pages).

METHODS AND SYSTEMS FOR ASSESSING PSYCHOLOGICAL CHARACTERISTICS

RELATED APPLICATIONS

This application is a continuation application of U.S. application Ser. No. 12/872,531, entitled "METHODS AND SYSTEMS FOR ASSESSING PSYCHOLOGICAL CHARACTERISTICS," filed on Aug. 31, 2010, issued as U.S. Pat. No. 9,558,499 on Jan. 31, 2017, which is a continuation-in-part of U.S. application Ser. No. 12/713,539, entitled "METHODS AND SYSTEMS FOR ASSESSING PSYCHOLOGICAL CHARACTERISTICS," filed on Feb. 26, 2010, and claims priority under 35 U.S.C. § 119(e) to U.S. Provisional Application Ser. No. 61/156,236, entitled "SYSTEM AND METHOD FOR ASSESSING AN EMOTIONAL STATE OF A SUBJECT," filed on Feb. 27, 2009, all of which are herein incorporated by reference in their entirety.

BACKGROUND OF INVENTION

1. Field of Invention

The present disclosure relates to psychological tests, and more particularly to systems and methods for eliciting and assessing the psychological characteristics of a test subject in relation to a research topic.

2. Discussion of Related Art

Many psychological tests exist which elicit and assess the reactions or responses of a person as they are exposed to stimuli. Such techniques typically involve, for example, presenting one or more images as stimuli to a test subject within the context of a particular topic of interest to the researcher. In response, the subject provides feedback indicative of their emotional state as he or she reacts to viewing the images. If given enough time, the feedback includes the effects of cognitive processing of each stimulus. The feedback is then analyzed according to one or more emotional or motivational theories to assess the psychological characteristics of the subject as they pertain to the topic.

SUMMARY

A method and system for eliciting and assessing an emotional response from a test subject is described herein. In one embodiment, a method for assessing psychological characteristics of a subject using responses obtained during the first moments of brain activity after presentation of a stimulus includes providing a context to the subject; exposing the subject to a visual stimulus for a first period of time of between approximately 500 milliseconds and approximately 1 second using a computer-implemented interface; receiving, responsive to the act of exposing, an input from the subject using the computer-implemented interface, the input to be received within one of the first period of time and a second period of time of no longer than approximately 300 milliseconds immediately following the beginning of the first period of time; and storing, responsive to the act of receiving the input, a user response that represents the pre-cognitive emotional reaction of the subject to the visual stimulus. The visual stimulus is selected by a processor from a plurality of visual stimuli stored in a database. The input received from the subject within the allotted time represents a pre-cognitive emotional reaction of the subject to the visual stimulus that is obtained during the first moments of brain activity after the act of exposing the subject to the visual stimulus. The method further includes repeating the acts of exposing, receiving, and storing for each of the plurality of visual stimuli, and determining, based on each of the stored user responses, one or more dominant emotional characteristics of the subject in relation to the context.

In another embodiment, the visual stimulus may be associated with one of a plurality of specific emotional reactions that the visual stimulus is known to evoke pre-cognitively. In another embodiment, the user response may further identify the one of the plurality of specific emotional reactions that is associated with the visual stimulus.

In yet another embodiment, the act of exposing the subject to the visual stimulus may include selecting, by the processor, the visual stimulus randomly from the plurality of visual stimuli.

In yet another embodiment, the context may include a stem sentence.

In another embodiment, the act of determining the one or more dominant emotional characteristics may be further based on a greatest number of stored user responses associated with the same one of the plurality of specific emotional reactions.

In another embodiment, the user response may include a response time, which is a period of time elapsed between the act of exposing the subject to the visual stimulus and the act of receiving the input from the subject.

In another embodiment, the method may further include an act of determining a motivational profile of the subject based on the one or more dominant emotional characteristics of the subject, wherein each of the one or more dominant emotional characteristics of the subject are linked to one of a plurality of motivational characteristics within a motivational model. The plurality of motivational characteristics may include security, empowerment, belonging, identity, engagement, nurturance, mastery, achievement, and esteem.

In one embodiment, the method may further include an act of assessing a value of at least one of a product and a service with respect to the subject based on the motivational profile of the subject.

In another embodiment, the method may further include an act of assessing a design of at least one of a product and a service with respect to the subject based on the motivational profile of the subject.

In yet another embodiment, the method may further include an act of matching the subject, based on the motivational profile of the subject, with at least one of a product, a service, a job, an individual, and a group of individuals using a website.

In yet another embodiment, the method may further include identifying, based on the motivational profile of the subject, an optimal advertisement to be presented to the subject.

In other embodiment, a system for assessing psychological characteristics of a subject using responses obtained during the first moments of brain activity after presentation of a stimulus includes a computer having a processor, a memory coupled to the processor, a display coupled to the processor, and a user input device coupled to the processor. The system further includes a presentation component for serially presenting, on the display, a plurality of visual stimuli to a user, each of the plurality of visual stimuli to be presented for no longer than approximately 1 second, each of the plurality of visual stimuli being associated with one of a plurality of specific emotional reactions that the respective one of the plurality of visual stimuli is known to evoke pre-cognitively during the first moments of brain activity following presentation of the visual stimulus to the subject. The system further includes a response component for receiving, on the user input device, one or more inputs from the user, each of the one or more inputs to be received no later than approximately 800 milliseconds after the respective one of the plurality of visual stimuli have been presented to the user, each of the one or more inputs representing a pre-cognitive emotional reaction of the user to the respective one of the plurality of visual stimuli. The system further includes an emotion assessment component for assessing one or more dominant emotional characteristics of the user based on each of the received one or more inputs.

In another embodiment, the system may further include a motive assessment component for assessing a motivational profile of the user based on the one or more dominant emotional characteristics of the user, wherein each of the one or more dominant emotional characteristics of the user are linked to one of a plurality of motivational characteristics within a motivational model.

In another embodiment, the system may further include a network interface coupled to the processor, wherein the network interface is used to communicate the motivational profile to a website provider. The website provider may be an e-commerce provider.

According to one embodiment, a computer readable medium includes computer-executable instructions that when executed on a processor performs the acts of exposing a subject to a visual stimulus for a first period of time of between approximately 500 milliseconds and approximately 1 second using a computer-implemented interface, the visual stimulus being selected by the processor from a plurality of visual stimuli stored in a database, the visual stimulus being associated with one of a plurality of specific emotional reactions; receiving, responsive to the act of exposing, an input from the subject using the computer-implemented interface, the input to be received within one of the first period of time and a second period of time of no longer than approximately 300 milliseconds immediately following the first period of time, the input representing a pre-cognitive emotional reaction of the subject to the visual stimulus that is obtained during the first moments of brain activity after the act of exposing the subject to the visual stimulus; storing, responsive to the act of receiving the input, a user response that includes the one of the plurality of specific emotional reactions that is associated with the visual stimulus; repeating the acts of exposing, receiving, and storing for the plurality of visual stimuli; and determining, based on each of the stored user responses, one or more dominant emotional characteristics of the subject in relation to a context for assessing a psychological characteristic of the subject. The computer-executable instructions may further include an act of determining a motivational profile of the subject based on the one or more dominant emotional characteristics of the subject, wherein each of the one or to more dominant emotional characteristics of the subject is linked to one of a plurality of motivational characteristics within a motivational model.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
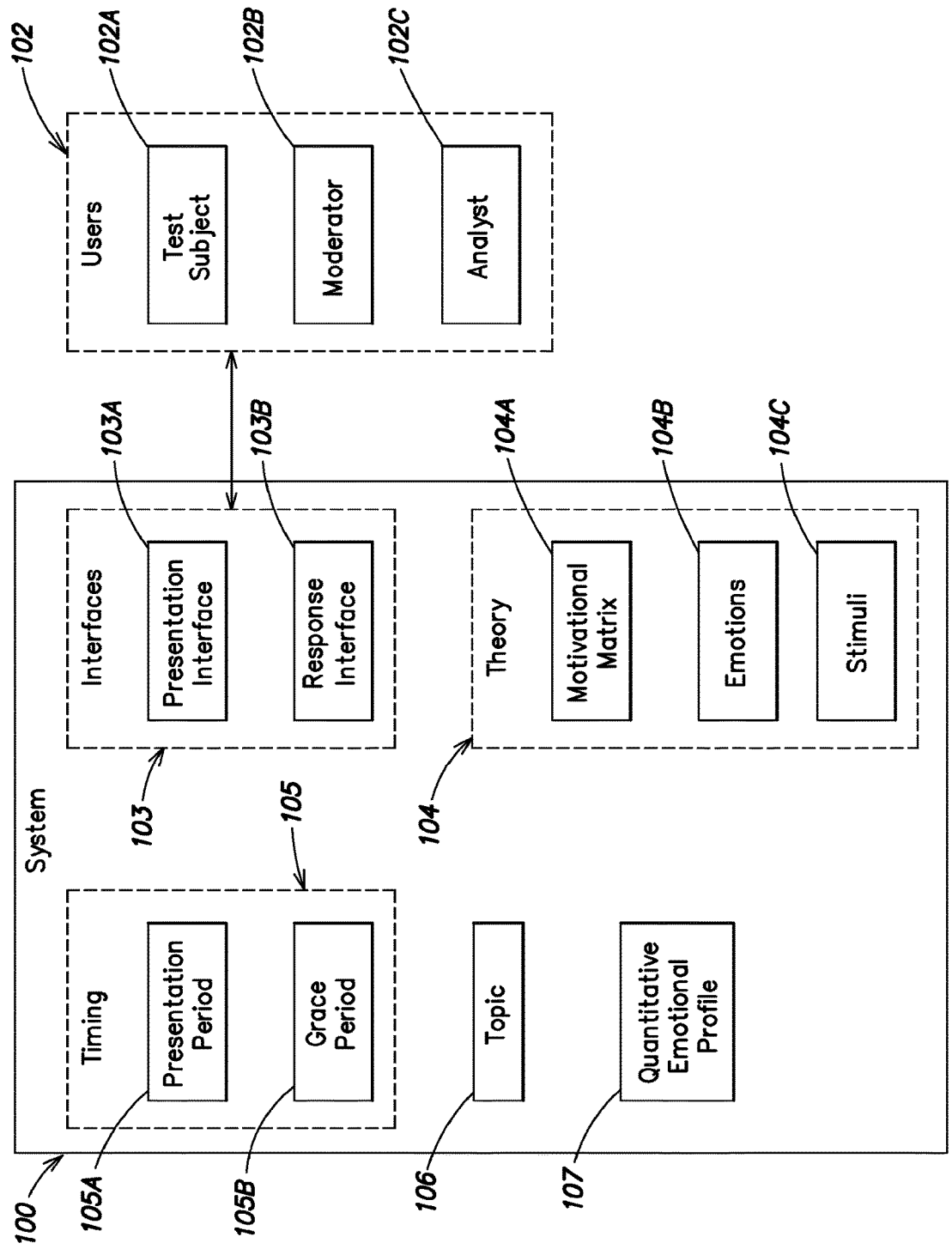
FIG. 1 illustrates an exemplary system for assessing psychological characteristics in which various embodiments of the disclosure may be implemented.

Embodiments of this invention are not limited in its application to the details of construction and the arrangement of components set forth in the following description or illustrated in the drawings. Embodiments of the invention are capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

An emotion, as used herein, is broadly defined an affective state of consciousness experienced by a person; e.g., affection, desire, fear, happiness, pride, etc. An emotional response, as used herein, is broadly defined as one or more characteristic emotive reactions by a person to one or more stimuli.

According to various embodiments, methods and systems for eliciting responses in a psychological test, and assessing psychological characteristics of a subject using responses obtained during the first moments of brain activity after presentation of a stimulus, are disclosed herein. It should be appreciated that because the response(s) to various stimuli elicited according to various embodiments of the present invention are representative of a pre-cognitive, neurological emotional reaction to the stimuli, assessments based on these responses are reflective of preconscious, deeply rooted psychological traits. This is in contrast to other techniques known in the art, wherein psychological assessments gained from longer periods of exposure and/or response time may be skewed or biased by the conscious or cognitive behavior of the subject, and therefore less reliable and less valid for identifying a person's true motives. It should also be appreciated that because the responses are of a preconscious nature, it is difficult if not nearly impossible for a subject to "game" or otherwise intentionally subvert the assessment by providing responses that are not representative of the subject's emotional reaction to the stimulus.

According to one embodiment, the stimuli used with the various techniques described herein are non-verbal (e.g., visual) stimuli. Non-verbal stimuli may be abstract with respect to the subject or topic being considered by the subject. For example, a photograph of a large airplane taking off in and of itself does not represent anything in particular. Such a photograph may represent power, freedom, human ingenuity, immenseness, "gravity defying feats," or any other association one might have with seeing a jumbo jet in flight. It is appreciated that using non-verbal stimuli inhibits the ability of a subject to provide artificially skewed emotional responses to the stimuli, or to otherwise intentionally subverting the test. Accordingly, responses to non-verbal stimuli may be more reliable for identifying the subject's true motivations with respect to a research topic.

According to another embodiment, a motivational profile of a subject is determined using the various techniques described herein. The motivational profile may describe one or more motivational characteristics of the subject. Further, the motivational profile may be used to identify designs of products and/or services that will have appeal to the subject based on the subject's motivational profile. For example, if one of the subject's motivational characteristics is safety, then products and/or services designed to appeal to safety-conscious consumers may also appeal to the subject.

In another embodiment, the motivational profile of the subject is used to match the subject with products, services, and/or people that appeal to or satisfy the subject's motive(s). In one example, the subject's motive may be used to identify a product or service (e.g., a car, job search) that appeals to or satisfies the subject. For instance, a subject having a motivational characteristic of security may be interested in purchasing a car having many safety features, while a subject having a motivational characteristic of empowerment may be interested in purchasing a sports or high-performance car. The subject's motive(s) may therefore be used to identify the products and/or services that the subject is most likely to purchase. In another example, if a subject's motivational characteristic is nurturance, then the subject may be matched with another person with a similar motivational characteristic (e.g., as in a dating or matchmaking service). In yet another example, the subject's motive may be used to identify advertisements, such as on a website, that offer products and/or services that are most likely to be purchased by the subject. For instance, the subject's motivational profile may be used as a keyword to search for relevant products and/or services on the Internet.

System Overview

FIG. 1 shows various interactions of a system 100 for assessing psychological characteristics according to various embodiments of the disclosure. As shown, there may be one or more types of users 102 of the system, including, but not limited to, one or more test subjects 102A, one or more moderators 102B, and one or more analysts 102C. Test subject 102A (or simply "subject"), as used herein, is broadly defined as an individual participating as an object of an experiment or test.

According to one embodiment, there may be only one test subject 102A participating in the test at any given time.

According to another embodiment, there may be multiple test subjects 102A participating in groups. In one example, responses of multiple test subjects 102A received during a test, performed in one particular context, may used to identify one or more psychological characteristics of the subjects under a "crowdsourcing" or distributed group collaboration theory. In another example, a focus group may be tested regarding a particular topic, and the results of the test may be used to validate the stimuli as to one or more associated emotional characteristics. The multiple test subjects 102A may participate at the same time or at different times, and may participate at the same location or at different locations.

Moderator 102B may be an individual who configures and/or administers the test to test subject 102A. According to various embodiments, moderator 102B may be responsible for selecting content that forms stimuli for the test, providing a context for the test, or providing other input to the test.

In another implementation, moderator 102B may provide instructions to test subject 102A, or may facilitate the test in other ways, including, for example, procuring the subject or interviewing the subject. Moderator 102B may be present with test subject 102A at the time the test is administered, although the test may be configured such that the test subject may participate outside of the presence of the moderator.

Analyst 102C may be an individual who reviews and/or analyzes the results of the test. Analyst 102C may be the same individual as moderator 102B.

One or more users 102 interface with the system 100 through at least two interfaces 103. A presentation interface 103A may include a display for displaying visual stimuli, such as images or words to one or more users 102. Presentation interface 103A may include a graphical user interface (GUI) or any other type of interface capable of presenting stimuli to a user. Presentation interface 103A may include other types of devices for presenting stimuli that evoke emotional responses, such as audio information.

A response interface 103B may be provided that includes one ore more input elements including a keyboard, mouse, button, touch screen or other input device type. In one example, the response interface 103B may be integrated into a smartphone, for example, Apple iPhone®, RIM BlackBerry®, or another device having similar capabilities. Response interface 103B may be coordinated with the presentation interface 103A, for example, as a control button displayed within the GUI. Response interface 103 may include devices to measure one or more physiologic functions of the test subject 102A, including, but not limited to, voluntary responses, involuntary responses, and biometric responses. It will be understood that the presentation interface 103A and the response interface 103B may be the same interface.

In one example implementation, a theory 104 for assessing the psychological characteristics of the test subject 102A includes a motivational matrix 104A, a plurality of emotions 104B, and a plurality of stimuli 104C. The motivational matrix 104A describes a psychological model of motives or aspirations of the test subject 102A, which various embodiments thereof will be described below. The plurality of emotions 104B includes one or more mental perceptions of the test subject 102A associated with an affective state of consciousness, various examples thereof which will be described below. The plurality of stimuli 104C includes sensory stimuli that, when presented to the test subject 102A, may elicit one or more of the emotions 104B from the test subject 102A.

In one embodiment, the motivational matrix 104A represents a psychological model describing nine core aspirations of the test subject 102A, arranged in two dimensions including a focus of aspiration versus a level of aspiration. The focus of aspiration may describe where the person is aspiring to improve their lives. For example, an intra-psychic focus describes how the person feels about oneself; an instrumental focus describes how the person feels about his/her activities; and an interpersonal focus describes how the person feels about his/her relationships with others. The level of aspirations may describe the desired emotional state of the person as he or she fulfills their aspirations. For example, "establishing potential" describes how a person feels when he/she believes that he/she possesses the ability to pursue his/her aspiration; "experiencing process" describes how a person feels when he/she is successfully progressing toward his/her aspiration; and "creating product" describes how a person feels when he/she has achieved his/her aspiration.

Figure 2:
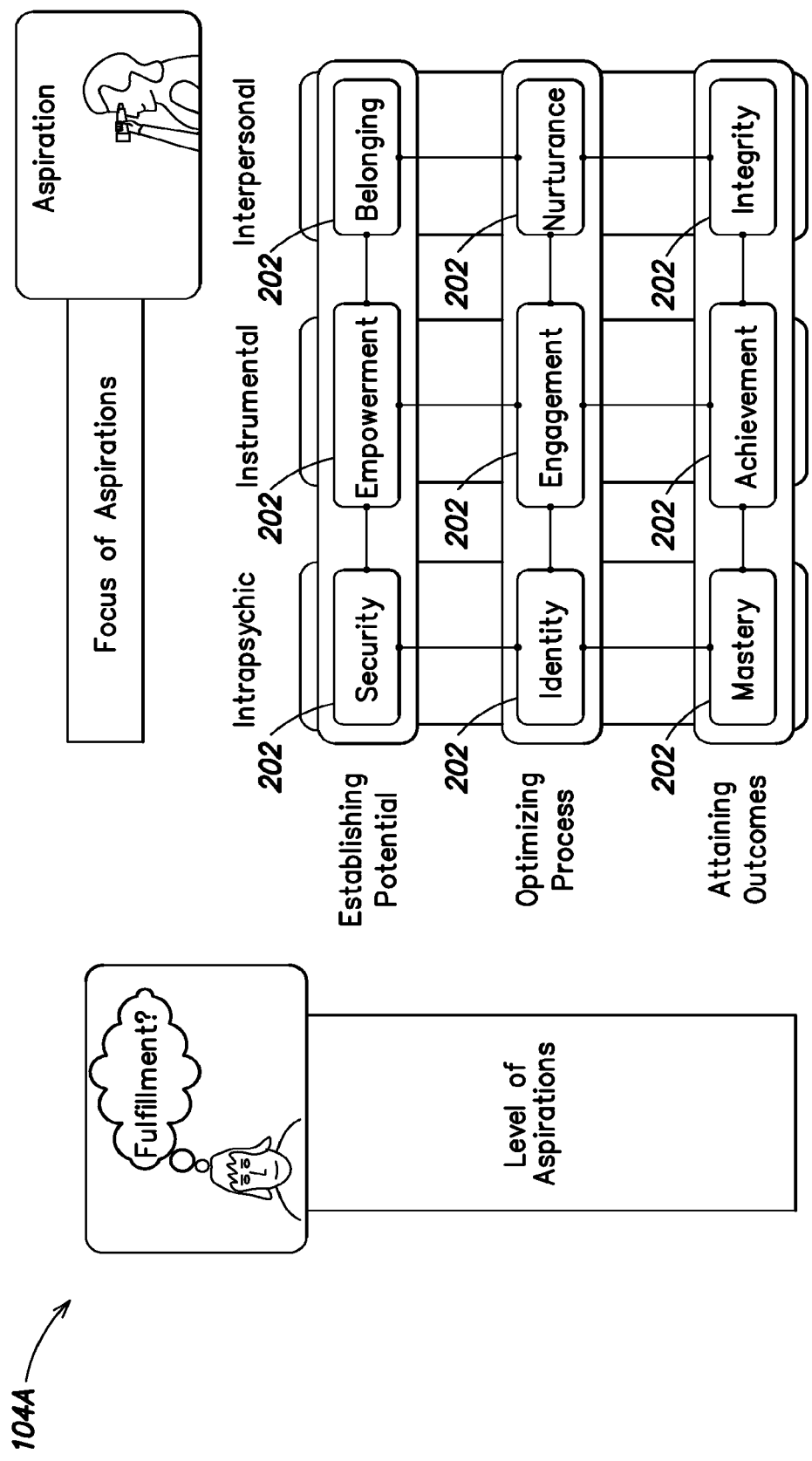
FIG. 2 illustrates an exemplary motivational matrix in accordance with one embodiment of the disclosure.

FIG. 2 illustrates an exemplary motivational matrix 104A consistent with one embodiment. The motivational matrix 104A includes nine motives 202, each motive 202 representing a combination of each focus of aspiration and level of aspiration, as described above, including security, identity, mastery, empowerment, engagement, achievement, belonging, nurturance, and integrity. In one example, "security" describes how a person feels when aspiring to establish potential within oneself. In another example, "achievement" describes how the person feels when aspiring to create a product through his/her activities. It will be understood that the motivational matrix 104A described herein is exemplary and that other motivational matrices may be developed to describe alternative psychological models.

Figure 3:
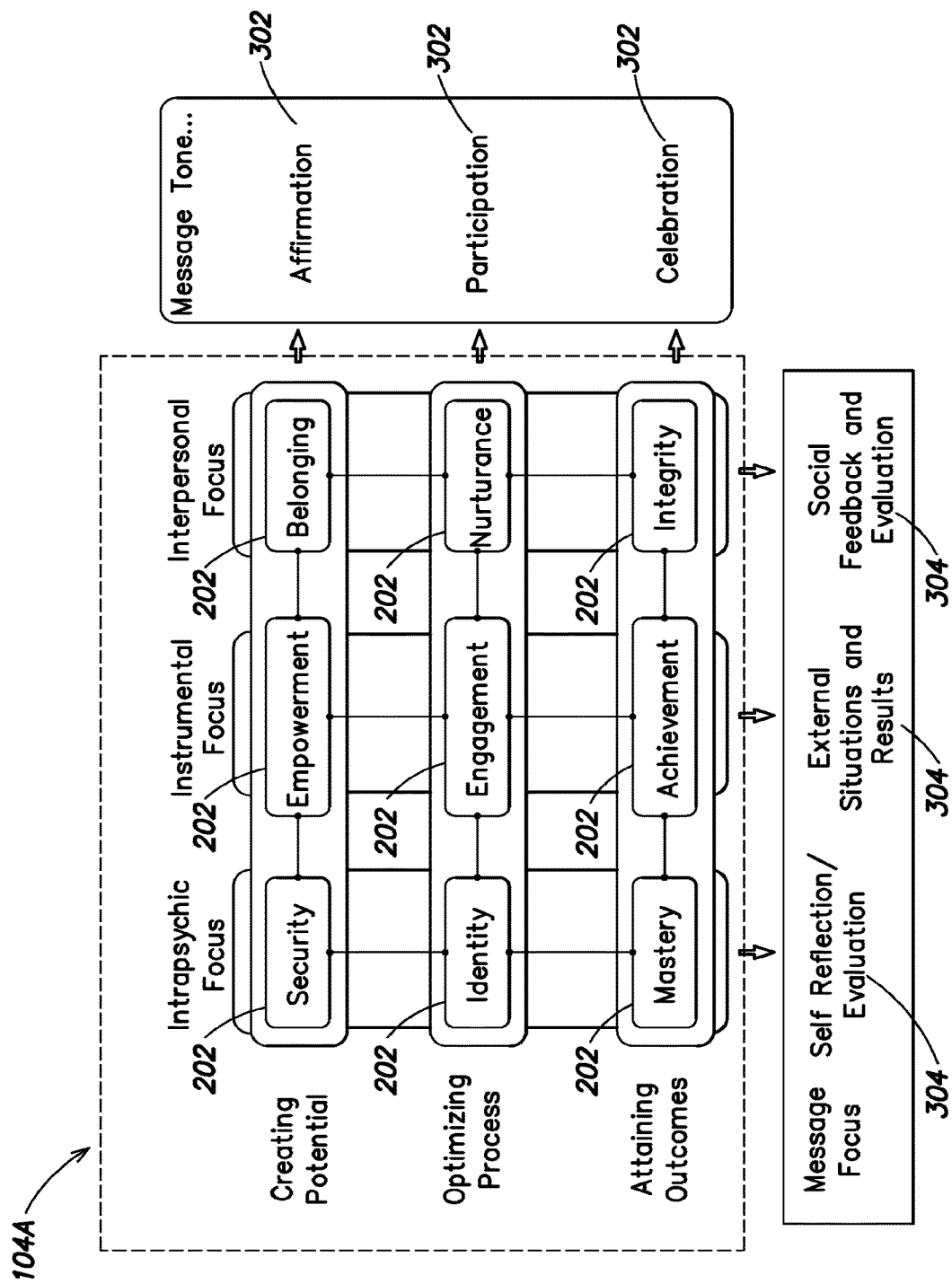
FIG. 3 illustrates an exemplary motivational matrix in accordance with one embodiment of the disclosure.

According to another embodiment, illustrated in FIG. 3, the motivational matrix 104A may be used to interpret the underlying motives 202 of the test subject and apply those interpretations. For example, a test subject having a motive of "engagement" may have a positive response a message having a participatory tone 302 and a focus 304 on attaining results. Messages, such as those for marketing a consumer product, may then be developed using this information, which may appeal to individuals having a similar motive.

According to various embodiments, each of the motives or aspirations described by the psychological model represent one or more emotions 104B experienced by the test subject 102A when the test subject 102A possesses the corresponding motive or aspiration and is exposed to an evocative stimulus 104C. For example, the emotions 104B may include feeling brilliant, superior, visionary, experienced, dominant, or excellent. Each of these emotions may, according to the model, be associated with the motive of mastery, as described above. Accordingly, when the test subject 102A possesses the motive of mastery, he/she is likely to experience one or more of the above emotions in response to certain stimuli 104C.

In various embodiments, the stimuli 104C may include, but are not limited to, images, sounds, smells, and other forms of sensory stimuli. Exemplary stimuli include images such as a person fastening an automotive seat belt, a fingerprint, a surgeon performing surgery, an airplane taking off, several business professionals working together, an athlete wearing a medal, children playing together, a mother tending to a sick child, and a military officer being decorated with ribbons.

The stimuli 104C may be classified by a type of stimuli. For example, images containing the color red may be classified as such. Any characterization of the type may be used, depending on the nature or character of stimuli being classified.

Each of the stimuli 104C may be associated with one emotion 104B, the emotion in turn corresponding to one motive in the motivational matrix 104A. For example: a person fastening an automotive seat belt evokes a feeling of security, a fingerprint (identity), a surgeon performing surgery (mastery), an airplane taking off (empowerment), several business professionals working together (engagement), an athlete wearing a medal (achievement), children playing together (belonging), a mother tending to a sick child (nurturance), and a military officer being decorated with ribbons (esteem). Accordingly, one of the stimuli 104C presented to a test subject 102A possessing one of the motives will elicit the emotion corresponding to the motive.

According to one embodiment, user 102 interaction with a test system (e.g., system 100) may be subject to certain timing attributes 105. For instance, one or more timing attributes 105 may control how long certain stimuli are presented to the user, and how responses should be, for example, received, validated, classified, and interpreted. In one embodiment, presentation period 105A may be defined that describes an amount of time a test subject (e.g., test subject 102A) is exposed to certain stimuli 104C through a presentation interface 103A. The amount of time may be determined based on a test theory. For example, one stimulus 104A may be presented to the test subject long enough for simple recognition of the stimulus to occur, but not so long that the test subject begins cognitive processing of the stimulus. In one embodiment, presentation period 105A may be between approximately 500 and approximately 1000 milliseconds.

According to one embodiment, test subject 102A may respond through the response interface 103B during presentation period 105A. A grace period 105B may also be defined that describes an amount of time a test subject may respond through response interface 103B after presentation period 105A has expired. Test subject 102A may be further exposed to the stimuli or a portion of the stimuli for at least a portion of the grace period 105B. For example, the grace period 105B may immediately follow the presentation period 105A and be up to approximately 250 milliseconds. Shorter or longer periods may be used that are also effective.

In one example implementation a topic 106 may be provided that indicates to the test subject a context for the test. For example, a topic may include a question regarding a particular subject matter, such as "How do you feel about (the particular topic)?" In another embodiment, a response to this question may be obtained by having the subject complete a sentence, such as "I wish I could feel more _____ about (the particular topic). The subject may, for example, perform sentence completions by selecting stimuli that evoke feelings that would be appropriate to fill the blank in the sentence. In one embodiment, topic 106 may be provided to the test subject 102A by the moderator 102B. In another embodiment, topic 106 may be provided to the test subject 102A through the presentation interface 103. In another embodiment, topic 106 may be provided to the analyst 102C by the moderator 102B, or vice versa.

As will be discussed in further detail below, the system 100 may generate a quantitative emotional profile 107. In one embodiment, the quantitative emotional profile 107 may be a quantitative measure of the emotional or motivational characteristics of the test subject 102A, including, for example, the emotion 104B experienced by the subject 102A and a strength of the emotion 104B.

Example Process for Assessing an Emotional Response

Figure 4:
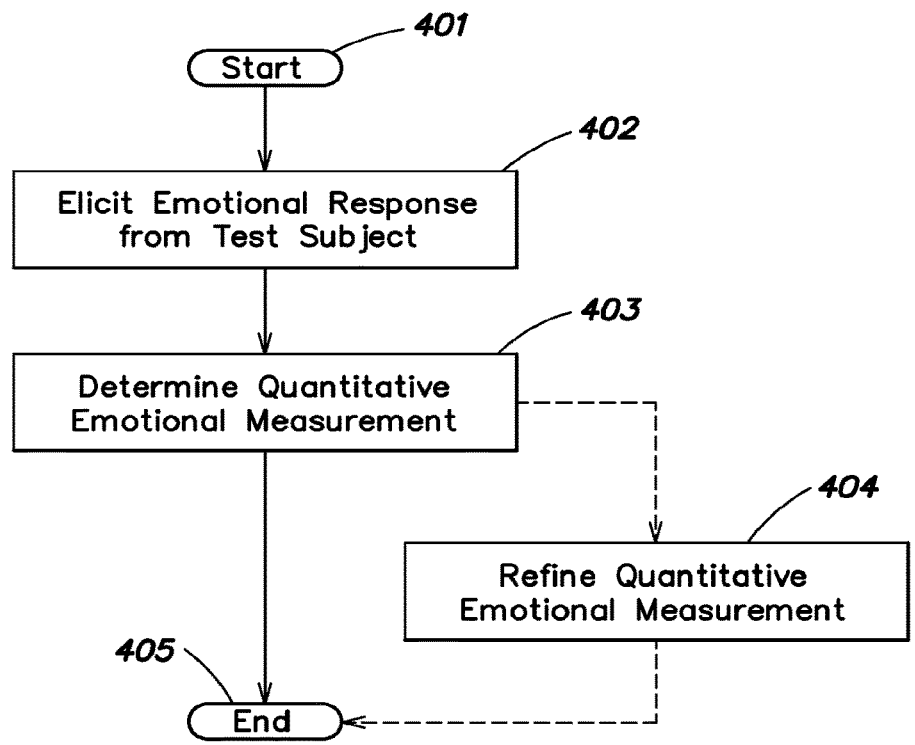
FIG. 4 illustrates an exemplary process for eliciting and assessing an emotional response from a test subject in accordance with one embodiment of the disclosure.

FIG. 4 illustrates a process 400 for assessing an emotional response from a test subject according to one embodiment.

Process 400 may be performed, for example, by the system 100 as discussed above with reference to FIG. 1. In one embodiment, process 400 includes eliciting an emotional response from the test subject and determining a quantitative emotional profile of the test subject based on the emotional response. Process 400 may optionally include refining the emotional quantitative profile of the test subject, for example, by subjecting the subject to further testing, questioning, or interviewing.

At block 401, process 400 starts. At block 402, an emotional response is elicited from a test subject, as will be described below with reference to FIG. 5. For example, act 402 may include establishing, in the mind of the test subject, a research topic to be considered while taking the test, such as a "matter at hand." Act 402 may further include providing, to the test subject, a directed inquiry, such as a "stem sentence." In one example, the research topic may be established by telling the subject that they will be "completing a sentence with a picture" and introducing the "stem sentence," for example, "I wish I could do my laundry in a way that made me feel more _____."

Additionally, act 402 may further include performing a stimulus test. The stimulus test may include, for example, presenting a series of visual stimuli in a rapid exposure sequence to the test subject through a computer implemented interface, as will be described below with reference to FIG. 6. One or more of the stimuli may provoke an initial emotional reaction in the test subject. In response to presenting one or more of the stimuli, feedback may be received from the test subject (e.g., through one or more interfaces), where the feedback includes a response indicative of the emotional state of the test subject in relation to the research topic. The feedback and a corresponding response time for each response may be recorded (e.g., by system 100) for analysis.

In one embodiment, act 402 may include performing, prior to the stimulus test described above, a "dial" or strength test, where the subject may be exposed to one or more stimuli (e.g., a video, advertisement, or speech) and asked to rate the strength of their feelings with respect to the stimuli on a scale of two or more strength values.

The subject may then be asked to complete a sentence, using the stimulus test described above. One exemplary sentence is "The reason I was very positive about this part [of the video or speech] is because it made me feel _____."

At block 403, a quantitative emotional profile of the test subject based on the feedback is determined. In various embodiments, the quantitative emotional profile represents the dominant emotional characteristics of the test subject, and the relative strengths of these characteristics, as elicited in act 402. If the stimuli selected by the test subject in act 402 have been previously associated with a particular emotion, the response and response time may indicate the presence and strength of the emotion in the test subject, where shorter response times indicate higher strength. Subsequently, the emotion represented by the selected stimuli, which may be classified according to the motivational matrix, may indicate the presence of the corresponding core motive. For example, if, among all the stimuli selected by the test subject, the majority of selected stimuli are classified into the motive of security, then the presence of the security motive in the test subject may be inferred.

After all images in the set have been presented, the resulting responses are tabulated and analyzed. Because each image is known to elicit a particular emotional characteristic, the dominant emotional characteristic of the test subject may be determined by analyzing the number of images selected having one particular emotional characteristic and the response time for each of those selected images. For example, if 45 images are presented, arranged in five cycles of nine images each, each of the nine emotional characteristics is represented by five different images. If the subject chooses more images representing one emotional characteristic than any other, and/or the subject chooses images representing one emotional characteristic more quickly than images representing other emotional characteristics, the subject is likely to harbor the one emotional characteristic as the dominant characteristic.

In another embodiment, the responses are used as a quality score or weighting that determines the nature (salience, strength, or quality) of the emotional response by the test subject. The weighting may be based on the number of responses received respective to a particular element of the motive matrix, or according to the respective response time. For example, responses having shorter than average response time may be given more weight than those having longer than average response time. Accordingly, responses having greater weight are likely to indicate that the subject harbors the emotional characteristic associated with the respective stimulus as the dominant characteristic. In another embodiment, this response time may be compared to response times for other stimuli, or for the same stimulus in other presentation conditions, to develop a score or weighting indicative of the quality of the response to the stimulus.

Optionally, at block 404, the quantitative emotional profile may be refined. For example, the test subject may be subjected to additional interviews and/or testing, including, but not limited to, a "linguistic expansion" test. The results of this refinement may be used to further assess the subject's emotional response according to the motivational model.

At block 405, the process 400 ends.

Example Process for Eliciting an Emotional Response

Figure 5:
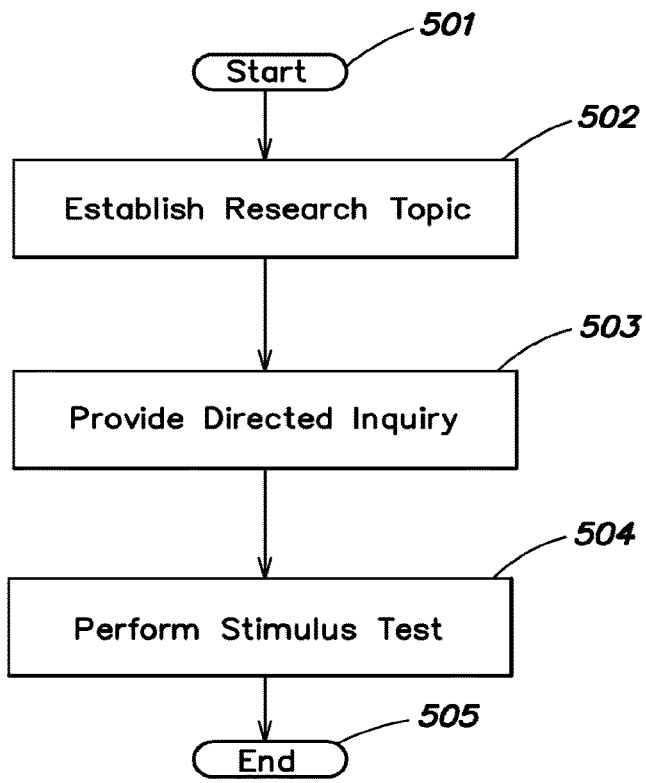
FIG. 5 illustrates an exemplary process for eliciting an emotional response from a test subject in accordance with one embodiment of the disclosure.

FIG. 5 illustrates a process 500 for eliciting an emotional response from a test subject according to one embodiment. Process 500 may be performed, for example, by the system 100 as discussed above with reference to FIG. 1. Process 500 starts at block 501.

At block 502, a research topic is established. The research topic may include any subject matter of interest to a researcher. For example, the research topic may include, but is not limited to, a consumer product or service, a retail establishment, a community, a job, a task, a leisure activity, or a political campaign. It will be understood that the research topic may include any subject matter, and more particularly, may further be directed toward ascertaining any subjective feelings that the subject may have towards the subject matter. The research topic may, for example, in the context of dishwashing liquid, direct the subject to consider the effectiveness, scent, color, toxicity, or other relevant characteristic of the dishwashing liquid.

Act 502 may include providing, to the subject, one or more prompts in a manner that communicates the research topic to the subject. For example, the subject is asked to consider a "matter at hand." The matter at hand provides a context for the test, and includes the subject matter for which the emotional state of the subject is to be elicited. The inquiry may be an incomplete sentence in the form of "Thinking about (a particular topic) makes me feel _____." For example, "Thinking about air fresheners makes me feel _____." For example, "Thinking about air fresheners makes me feel _____."

At block 503, the subject may be provided with a second prompt to direct them to a specific emotional target within the matter at hand, for example, a stem sentence. The subject may be instructed to select stimuli that he or she most closely associates with the emotion completing the stem sentence. The stem sentence may be, for example, a "fill-in-the-blank" type prompt in the form of "When I use (a particular topic) I am trying to make myself feel more (or less) _____." For example, the subject may complete the stem sentence by thinking, "I wish there was an air freshener that would make me feel more relaxed." Subsequently, if the subject is exposed to a stimulus that he or she associates with relaxation, he or she may select that stimulus in response.

In another embodiment, the subject may be presented with a "fill-in-the-blank" type of prompt in the form of "When I use (a particular topic) I am trying to make myself feel more/less _____." The subject may be presented with two sets of stimuli (e.g., images), one set representing positive stimuli evoking a positive response, and one set representing negative stimuli evoking a negative emotional response, and instructed to choose those stimuli that evoke emotions that are stronger ("more") or weaker ("less") in accordance with the prompt.

After establishing the research topic, at block 504, a stimulus test is performed on the test subject, one embodiment of which is described below with reference to FIG. 6. At block 505, the process 500 ends.

Example Process for Performing a Stimulus Test

Figure 6:
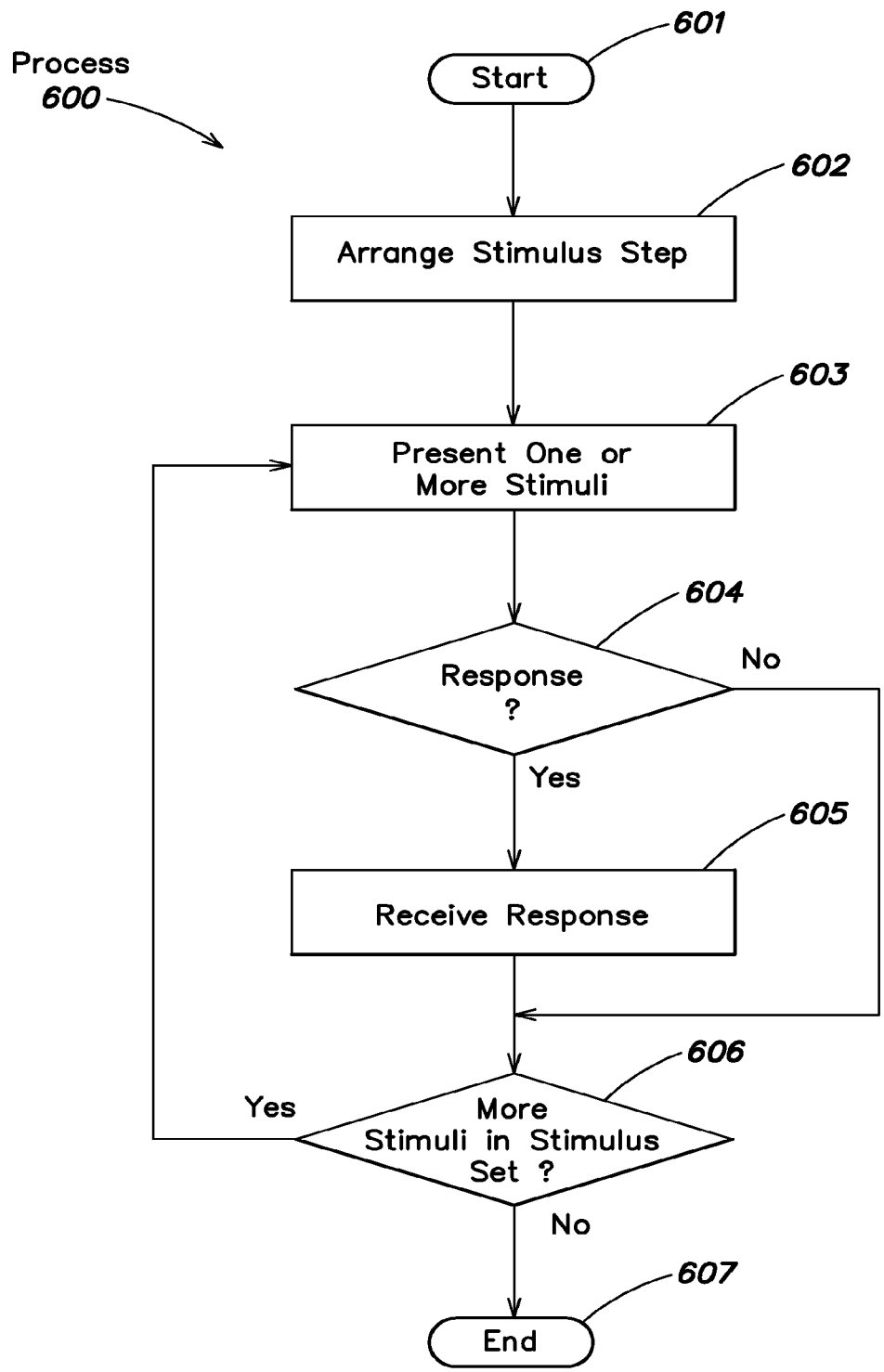
FIG. 6 illustrates an exemplary process for performing a stimulus test according to one embodiment of the disclosure.

FIG. 6 illustrates a process 600 for performing a stimulus test according to one embodiment. At block 601, the process 600 starts. At block 602, a stimulus set including non-verbal stimuli is arranged. The stimuli may be images. However, a non-exclusive list of non-verbal stimuli in the stimulus set includes images, sounds, colors, smells, and the like. According to one embodiment, it is appreciated that one disadvantage of prior techniques is that they are not consistently able to provide access to thoughts and feelings that may be below the threshold of subjects' conscious awareness. It has been established in some psychological research that areas of the brain responsible for emotional reactions and emotional memories are distinct from areas of the brain responsible for conscious thought. It has also been established that images can perform a projective or enabling function, allowing research respondents to gain access to emotions or ideas that are below the threshold of consciousness, or allowing respondents to articulate feelings or thoughts that they might otherwise be unable to articulate.

Figure 7:
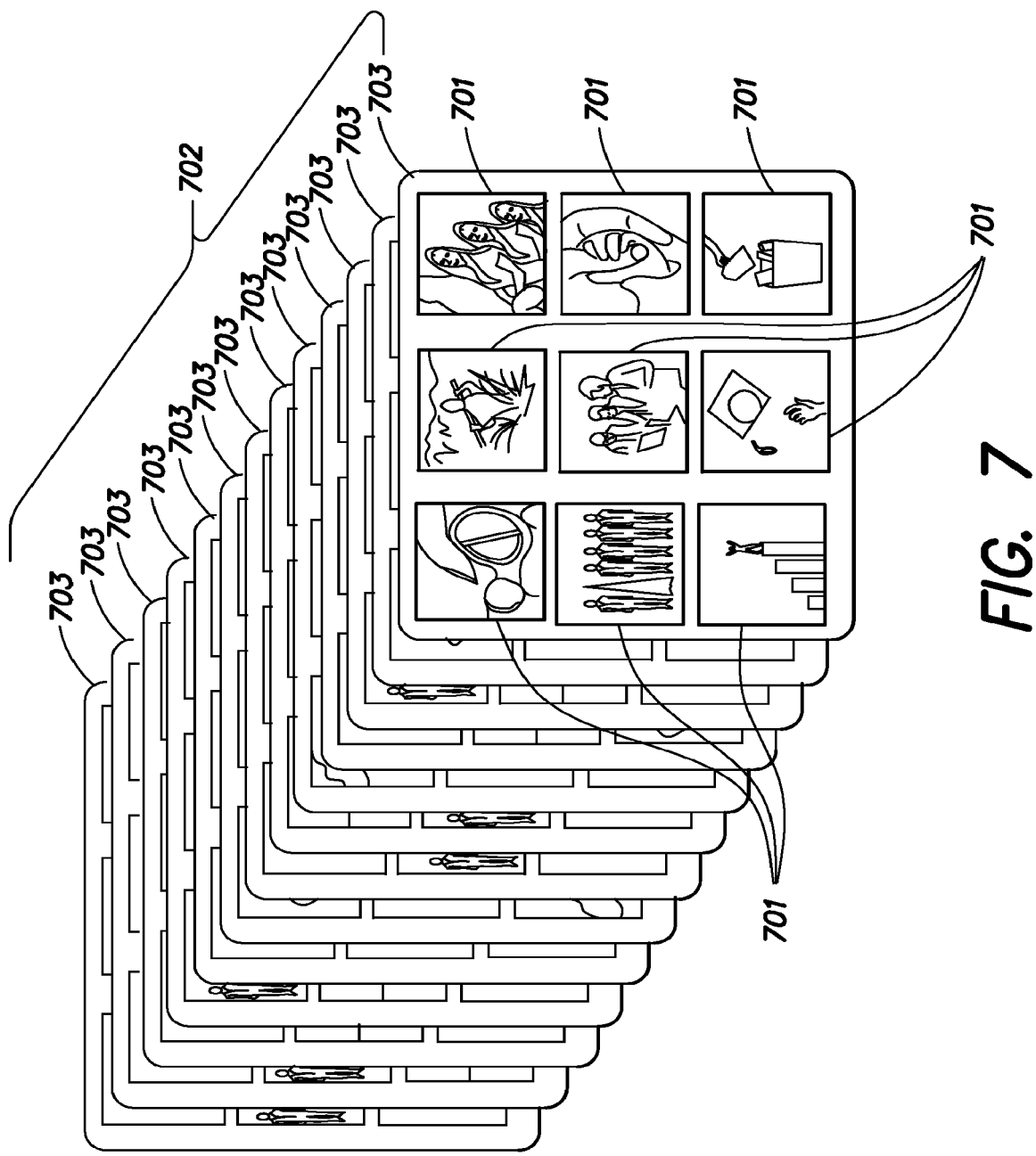
FIG. 7 illustrates an exemplary stimulus set in accordance with one embodiment of the disclosure.

An exemplary stimulus set is shown in FIG. 7. Each image 701 is known to elicit a particular emotional characteristic from an individual. Each image 701 may be classified, for example, according to a motivational model comprising a matrix of motives, or may be used for raw comparisons between different test subjects. The matrix may contain a plurality of elements, each representing a different motive. For example, a non-limiting matrix of motives 104A, as shown in FIG. 2, may include security, empowerment, belonging, identity, engagement, nurturance, mastery, achievement, and integrity, arranged by focus of aspiration versus level of aspiration. Thus, each image 701 in the set may be associated with one of the motives in the matrix represented by the model. Classification of images 701 may occur before the test begins, or the images may be classified dynamically as the test proceeds. For example, images which have strong quantitatively validated emotional associations with each of the motives may be used. When these images are selected by the test subject, the images reliably indicate the presence of the associated motive in the test subject. In another example, images may be classified into a pre-selected matrix of motives and validated through testing. In yet another example, images selected most often by a group of test subjects in a similar context (e.g., using a crowdsourcing approach) may be classified into one or more emotional states or motives based on the context.

In one embodiment, as shown in FIG. 2, the matrix 104A may comprise nine elements; however, it will be understood that the number of elements in the matrix may vary according to the particular motivational model being utilized for the research. The image set 702 comprises at least one image for each element in the matrix. For example, in a matrix having nine elements, the image set 702 contains at least nine images. In one embodiment, each element of the matrix is represented by an equivalent number of images 701 in the set; for example, in a matrix having nine elements, the image set 702 may contain nine, 18, 27, 36, 45, or higher multiples of nine images. In this manner, the subject is given multiple opportunities to respond to images eliciting the emotion that the subject is experiencing, and the results of the test are improved. Each image may be included in the set once.

According to one embodiment, it is appreciated that a reaction by the test subject to the presentation of a visual stimulus includes the evocation of an emotional response to the stimulus before extensive cognitive processing (other than simple recognition) of the stimulus begins. In one embodiment, this period of "pre-cognitive" processing has been observed to be approximately 500 milliseconds to one second in length. Insights about psychological processing time and psychological processing sequence may be leveraged to develop a range of diagnostic procedures that carefully controls a total time of stimulus exposure before a response from a subject, and thus eliminates or strictly limits time for conscious processing before a response is made. The diagnostic procedures include tests having very short stimulus exposures (less than approximately one second), as well as tests with longer periods of exposure, which may be used separately and in combination as part of a diagnostic assessment.

Referring again to FIG. 6, at block 603, the subject is presented with a series of stimuli in rapid succession. In one embodiment, images 701 are presented through a computer implemented interface, such as a display. For example, each image 701 in the image set 702 may be presented, during a test, to the test subject in a random order to avoid enabling a test subject to predict a particular sequence through familiarity gained during testing.

In one embodiment, each image 701 in the image set 702 is presented once during the process 600. One "cycle" of images 703 includes one image 701 for each element of the motive matrix. If the image set 702 contains more than one image 701 for each element of the motive matrix, then one cycle of images 703 may be presented before the next cycle 703 begins; however, the order of images 701 presented within each cycle 703 may be random.

At block 604, if exposure to any stimulus in the series provokes an emotional response that the subject associates with the topic, the subject is forced to quickly indicate this by selecting the stimulus during the presentation period or within a short time thereafter referred to as the grace period. The subject indicates his or her selection, or emotional response, to each stimulus in the series through a second computer interface, which may include a button, keyboard, mouse, or other such device. Responses from the test subject may be received in the form of a positive or negative response to each image. A positive response may be, for example, one in which the test subject responds favorably to viewing the image, or one in which the test subject has a significant or strong emotional association with the image. A negative response may be one in which the test subject responds unfavorably to viewing the image, or one in which the test subject has little or no emotional association with the image.

The responses may include one or more values representing the strength or quality of the test subject's emotional state as elicited by each image. For example, the test subject may quantify his or her emotional state as being strong, moderate, or weak. The list of responses may include one or more values representing one or more behaviors (e.g., a button press or a screen touch) it may also include one or more of these behaviors in association with one or more physiologic states in relation to each image, such as (but not limited to) brain blood flow, resistance, temperature, motion, audible measurement, and heart rate.

At block 605, a response to each of the stimuli may be received and recorded along with a reaction time. The resulting data may be tabulated and analyzed by a software program that characterizes a dominant emotional state of the subject. Biometric feedback, including pulse, blood pressure, eye movement, and the like, may also be collected from the subject.

At block 606, if there are stimuli in the set that have not yet been presented, the process 600 returns to block 603. Otherwise, process 600 ends at block 607.

According to another embodiment, each of the stimuli selected by the test subject during process 600 may be presented again to the subject in rapid succession. Biometric feedback may be collected and measured during the presentation to obtain additional information about the strength of feeling about each stimulus by the subject. The feedback may be used to refine the quantitative emotional profile of the subject.

Example Timing Sequence

Figure 8:
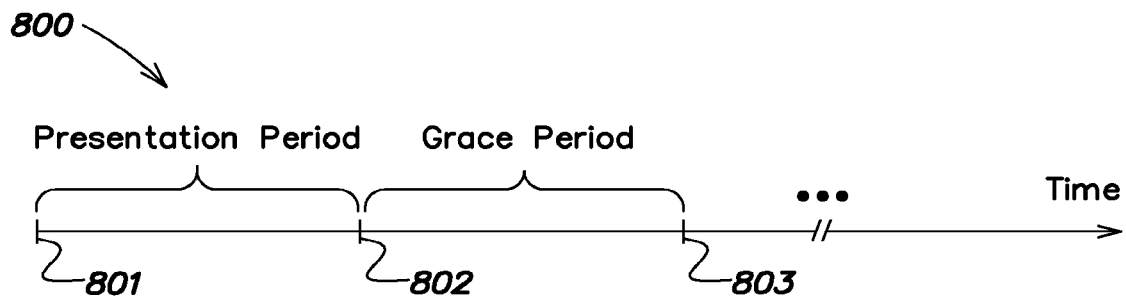
FIG. 8 illustrates an exemplary timing sequence in accordance with one embodiment of the disclosure.

FIG. 8 shows a timing sequence 800 in accordance with an embodiment of the disclosure. Starting at 801, each image is presented for approximately 500 milliseconds to 1 second (the "presentation period"). At the end of the presentation period 802, an optional "grace period" begins. During the grace period, the image may be removed immediately, or gradually, from the test subject. For example, the image may be wiped or faded from view over the course of at least a portion of the grace period. In another example, a progress bar may be displayed to indicate an amount of time remaining until the grace period ends. The grace period may be approximately zero to 250 milliseconds immediately following the presentation period. The grace period ends at 803.

In another embodiment, the visual stimulus is removed after display for a predetermined time, after which the test subject is permitted to respond. In this way, the test subject is permitted to respond after the visual stimulus is shown, but the visual stimulus is removed so that only the emotional response is measured. In another embodiment, the stimulus may be shown after a second image (to "prime" the response) or before a second image (to "mask" the impact of the stimulus).

The timing sequence 800 may repeat for each image in the image set. Shorter or longer periods may be used that are also effective.

Example Process for Receiving Test Responses

Figure 9:
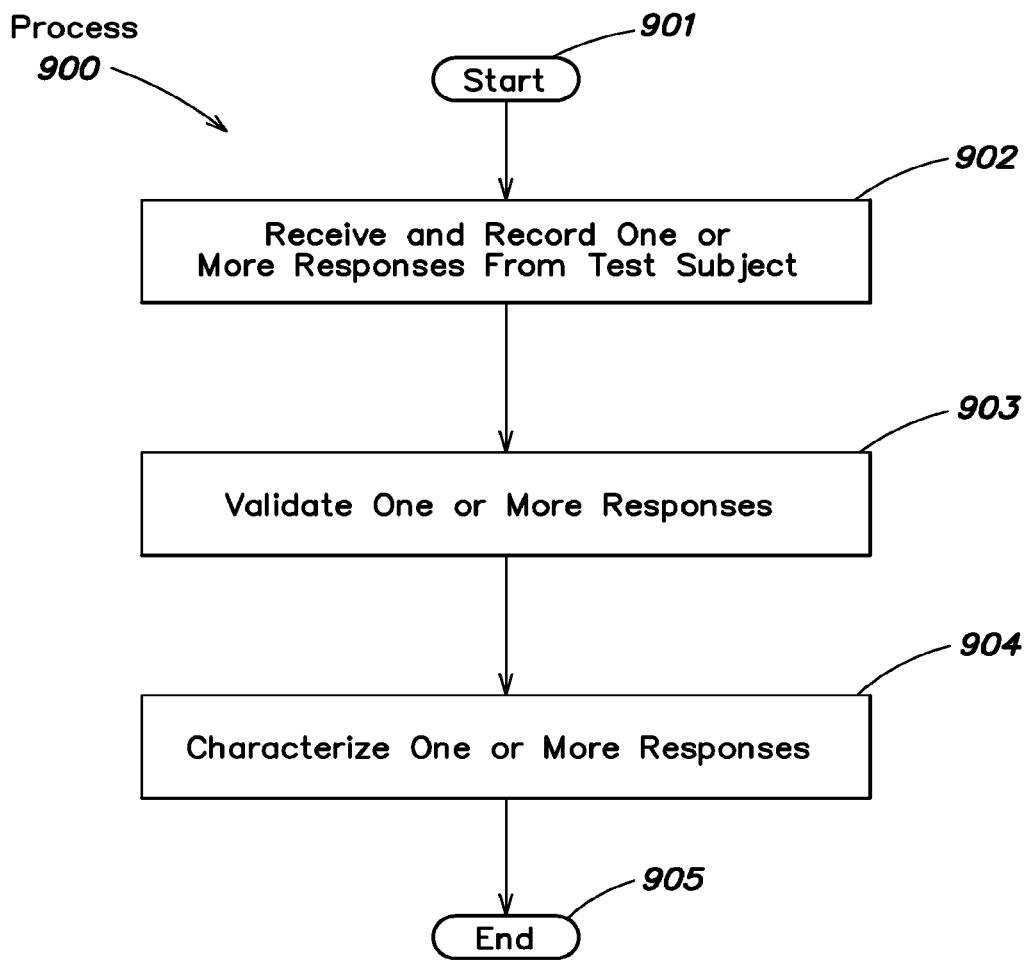
FIG. 9 illustrates an exemplary process for receiving one or more responses from a test subject in accordance with one embodiment of the disclosure.

FIG. 9 shows a process 900 for receiving one or more responses from the test subject in accordance with one embodiment of the disclosure. For example, process 900 may be implemented in accordance with process 600 as shown in FIG. 6 and discussed above. At block 901, the process begins. At block 902, the subject, via a user interface, may react or respond to each image by, for example, selecting a button (e.g., by clicking a mouse) during the presentation period or the grace period, if any. It will be understood that other methods of responding may be utilized, for example by pressing a key, touching a screen, speaking or shouting, shaking or pointing a motion-sensitive device, etc. Responses received outside of the presentation and grace periods may be invalid as to the respective stimulus. The response, if any, to each image is recorded along with a response time which is measured from the time when the image is first presented until the time when the response is received.

At block 903, the responses may be validated. If a response is received less than approximately 150 milliseconds after the stimulus is presented to the subject, it is unlikely that the subject has had an adequate amount of time to recognize and react to the stimulus in a meaningful manner Rather, a response received in such a short amount of time may be an erroneous response, or an attempt by the test subject to subvert the test, and as such may not be useful for assessing the subject's emotional characteristics reliably. Likewise, a response received more than 300 milliseconds after the presentation period ends is likely to occur after the subject has had an opportunity to consciously process the response, and accordingly may be of marginal value in the assessment of the subject's emotional characteristics. Responses having response times in these ranges may be characterized as invalid or an attempt by the subject to subvert the test, depending on the context of the test. For example, during a job interview, the subject may have a reason to subvert the test if he or she believes that doing so might improve the chance of obtaining employment.

At block 904, the responses may be characterized. If the subject responds to none of the stimuli, there is no useful information for assessing the subject's emotional characteristics. Likewise the results of the test are likely to be skewed if the subject responds to the stimuli in a predictable pattern, for example by selecting every third image in the sequence or in a repeated pattern, selecting images randomly, selecting only images containing a certain color or object, or selecting all images in the set. It will be understood that other methods of characterizing the responses exist.

At block 905, process 900 ends.

Other Examples

Another embodiment of the method may further include comparing a quantitative emotional profile of the test subject with a quantitative emotional profile of other test subject(s). For instance, this may be useful to determine how similar an emotional state of one subject is to another subject or group of subjects. Results from the same subject at different points in time—or at different places—can be used to describe emotional changes in a subject across points in time or across different locations.

In one embodiment, large numbers of responses to large numbers of stimuli are collected and presented using any of the presentation methods described above, for example, using a crowd-sourcing approach. Statistical analysis of these responses would be used to identify "clusters" of responses within the overall dataset, indicative of predominant emotional states within the large group overall, or within subgroups of the total group. This technique could be used to describe the nature of these emotional states in detail based on the individual responses which fall into a response cluster, or on the responses which fall most closely to the statistical center of a response cluster.

In one embodiment, visual stimuli testing techniques are combined with interviews (e.g., psychological interviews, job interviews, police interrogation, etc.). Because a subject's emotional state can be assessed quickly and accurately, an interviewer may use the method prior to or in association with an interview to identify lines of questioning that the interviewer should take (e.g., if an emotion detected is to fear, then asking probing questions of the subject related to fear).

In one embodiment, lists of emotional descriptor terms are presented, in a linguistic expansion test, to the subject in a further assessment battery as a means for further defining emotions that are revealed in the visual stimulus exercise. Responses to these lists of terms can be analyzed statistically in real time to determine which of the terms are most accurate descriptors of the subject's emotional state as revealed in the image exercise. In one embodiment these terms may be presented in a forced choice exercise to obtain ranking of terms that are most descriptive of the emotional state. In another embodiment, these terms may be presented in rapid sequence with respondent choosing words that describe an emotional state indicated by images previously chosen.

Another embodiment of the method may include assigning descriptive names to each one of the visual stimuli. The method may further include comparing the positive and/or negative selections by the test subject with the descriptive names to determine the emotional state of the test subject.

Another embodiment of the method may also include classifying of emotions into a set of two or more emotion classes. Classifying the set of emotions may include creating multiple stimulus cue lists. The cue lists may be arranged into groups, where each group represents a different emotional state. One or more sets of stimuli may be presented to the subject to test for particular emotion classes. The stimulus selection patterns of the test subject may be correlated with an emotional state by indexing the stimuli selected by the test subject into the emotion classes. In one example, there may be nine sets of images, each of which sets includes an image relating to a particular emotion class. If the subject selects the images from one particular emotion class more frequently than other emotion classes, then the subject is more likely to feel the emotional characteristic of the emotion class.

Another embodiment of the method may relate to using such visual stimuli testing methods along with interviews (e.g., psychological interviews, job interviews, police interrogation, etc.). Because a subject's emotional state can be assessed quickly and accurately, an interviewer may use the method prior to or in association with an interview to identify lines of questioning that the interviewer should take (e.g., if an emotion detected is fear, then asking probing questions of the subject related to fear).

Another embodiment of the method relates to a computer system that is capable of performing different embodiments as disclosed herein.

Classifying Stimuli

In one embodiment, stimuli may be classified according to a motivational model by presenting a list of classified stimuli comprising, for example, words, terms, phrases, images, smells, shapes, substances, textures, or colors to multiple test subjects. Each stimulus in the list has a known or hypothesized relationship with one emotion. These relationships may be vetted by experts analyzing the stimuli, or through research and testing. The test subjects may select one or more of the stimuli in the list relative to an established motive. For example, if the motive is security (of, e.g., their home), the test subjects are asked to select stimuli that elicit emotions that evoke feelings of security at home. Stimuli most often selected by the test subjects are thus validated against the model and useful for future testing, while stimuli that are less often or not selected are presumed to be not representative of the motive.

Another exemplary process for classifying stimuli (e.g., images) is to provide one or more investigators with a set of image cues with instructions to find related images at their best discretion by searching, for example, their environment, a library, or the Internet. The images which are found are then tested and validated by exposing the images to a large sample, asking each respondent in the sample to match each image with an emotional category, and selecting those images where a statistically significant majority of respondents associate a particular image with a particular emotion. Validation may be performed, for example, across an entire matrix simultaneously, or, on a single matrix dimension at a time.

Another exemplary process for classifying images includes inserting prospective emotive images into a sequence of classified images during a stimulus test performed in accordance with embodiments of the present disclosure. The prospective images may be classified by association using any of the comparison methods described herein. For example, in a set of five images each representing one emotion, three of the images are vetted and two are not. If multiple test subjects exposed to all five images select either or both of the unvetted images along with one or more of the vetted images, the unvetted images can be vetted or classified using statistical analysis of the cumulative selections by all test subjects. Over a period of many tests and a variety of topics a valid classification of the image may emerge.

According to another embodiment, a comparison of emotional responses by multiple individuals to various stimuli may be performed using a "crowd-sourcing" theory. For example, the individuals may select images of products that have emotional appeal to them, e.g., an individual may be asked to select their favorite type of literature by selecting from a group of books including books that the subject has looked at and books that other subjects have looked at. Over time, one or more clusters of images representing the collective responses of the individuals are formed. The cluster(s) may be statistically analyzed to identify a common emotional theme among the images, which may then be classified according to that emotion.

Testing System

Figure 10:
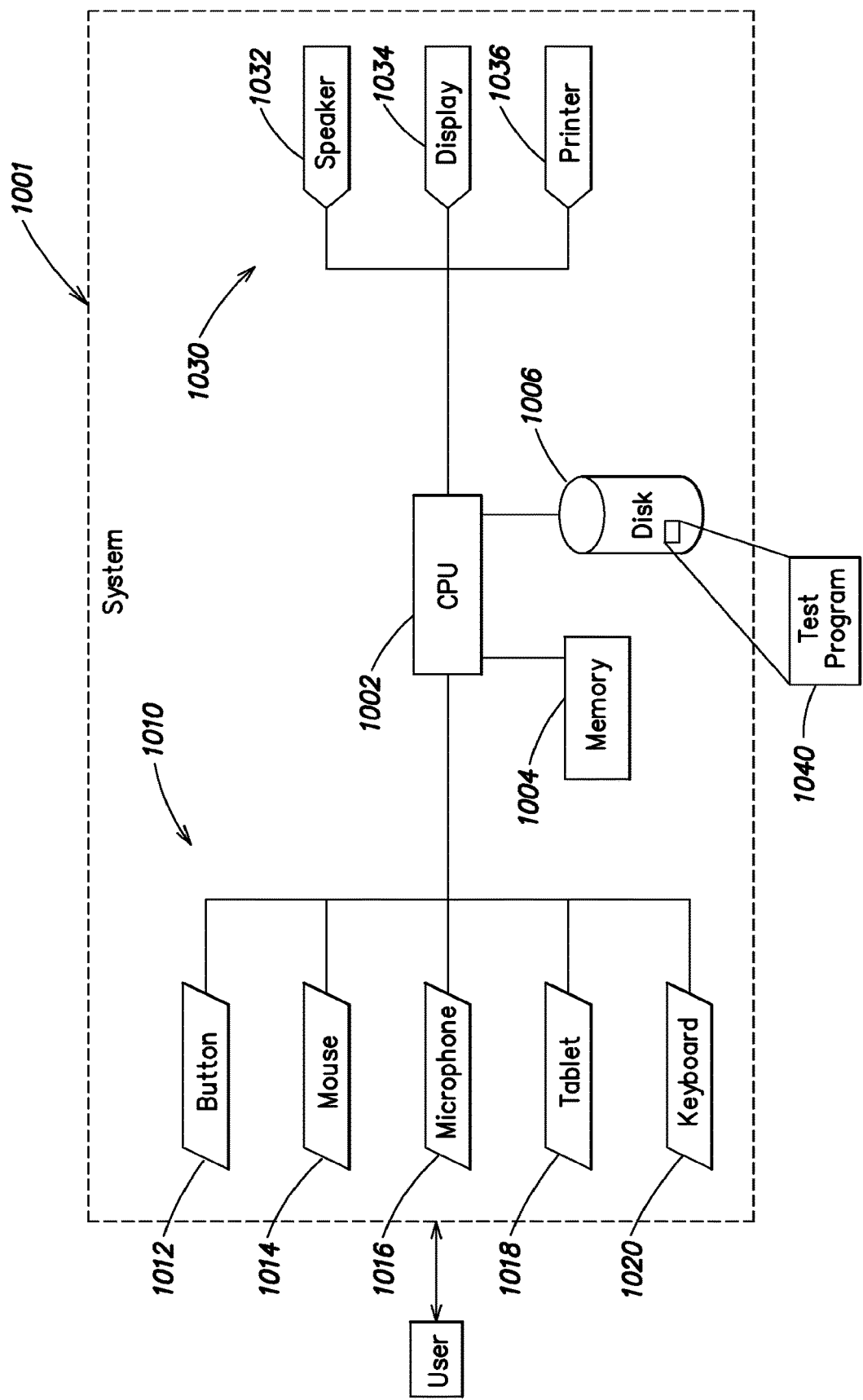
FIG. 10 illustrates an exemplary system in which various embodiments of the disclosure may be implemented.

FIG. 10 shows an exemplary system architecture of the present disclosure, which is generally indicated at 1001. A central computer 1002, or CPU, is connected to memory 1004 and disk storage 1006. A nonexclusive list of input devices, generally indicated at 1010, are connected to the CPU 1002, including (but not limited to) a button 1012, a mouse 1014 or similar pointing device, a microphone 1016, a tablet 1018, and a keyboard 1020. A nonexclusive list of output devices, generally indicated at 1030, are also connected to the CPU 1002, including (but not limited to) a speaker 1032, a display 1034, and a printer 1036. It should be appreciated that a computer system used to implement various embodiments of the present invention may include other types of input/output devices or have a different architecture than the computer shown.

One embodiment of the invention may be embodied by software stored on a computer-readable medium (e.g., a memory, storage, disc or other medium), and executed by one or more computer systems. In one embodiment, a test program 1040 is stored on the disk 1006. For instance, various embodiments can be executed by a computer system having an architecture as shown in FIG. 10.

Figure 11:
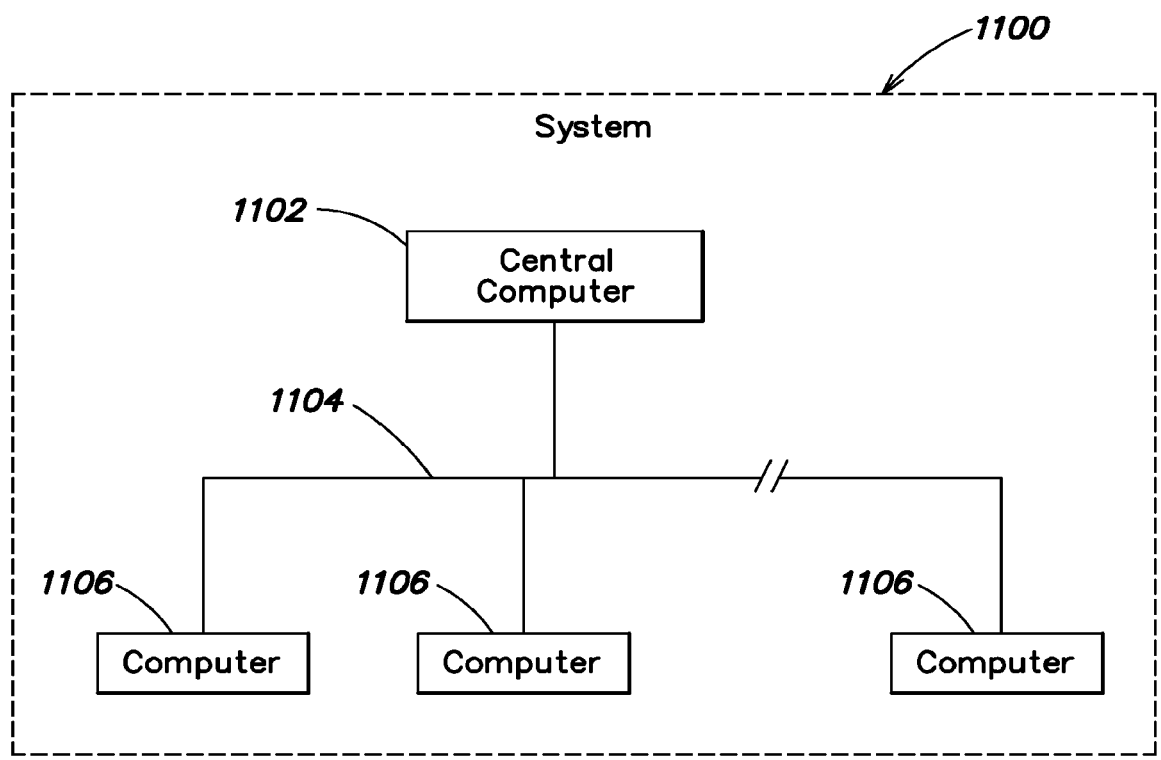
FIG. 11 illustrates an exemplary system in which various embodiments of the disclosure may be implemented.

Referring to FIG. 11, an exemplary system architecture of a distributed testing system in accordance with the present disclosure is generally indicated at 1100. A central computer 1102 is connected to a wired or wireless network 1104. One or more fixed or portable computing systems 1106 are also connected to the wired or wireless network 1104, so that they may communicate with the central computer 1102. The types of computing systems 1106 may include, but is not limited to, handheld personal digital assistants (PDAs), desktop personal computers (PCs), laptop PCs, tablet PCs, game controllers, "smart" phones, and the like. In one example, responses from one or more respondents in a focus group session or in a survey may simultaneously gathered using the computers 1106 (e.g., a cell phone, PDA, tablet computer or other type of portable computer system) connected wirelessly to the central computer 1102 over the network 1104. The central computer 1102 may analyze the responses in real time and provide further outputs to be presented to a moderator and/or each respondent for further probing and discussion among the focus group.

In another example, focus group interviews may be conducted whereby a moderator and one or more respondents utilize computers 1106 connected to the central computer 1102 over a network 1104. In one embodiment, the system allows all members of the group to make inputs simultaneously to a single database or a single computerized "object" (e.g., a photo collage) stored in memory or on disk utilizing one or more input devices. In conjunction with output devices, all members of the group may work with the results generated collectively by the group as a basis for continued discussion and reflection.

In another example, focus group interviews are conducted where a third party may observe and/or participate in the research in real time. A moderator, the third party, and one or more respondents utilize computers connected to the central computer over the network. For instance, computers may be any type of computer systems as discussed above, including, but not limited to, portable computers such as laptops, cell phones, PDAs, or other types of computer systems. The system allows all members of the group to make inputs simultaneously to a single database or a single computerized "object" (e.g., a photo collage) stored in memory or on disk utilizing one or more of the input devices. In conjunction with output devices, all members of the group may work with the results generated collectively by the group as a basis for continued discussion and reflection.

Utilizing the exemplary system architecture described above in FIG. 11, several applications of the present disclosure may be implemented. In one example, the disclosed method may be used to expose photo-stimuli (for, e.g., a one second exposure time or similar period sufficient to invoke an emotional response, but not to give the respondent time to form a well-thought response) to force emotionally-driven selections of photos that associate with the emotional states of the respondents. Photo selections made by all members of a focus group are scored by the total number of votes, and by the speed of selection (response time) to generate a list of "most salient" stimuli that are probed in more detail to uncover information about emotional states.

Example Applications

The following is a non-limiting list of applications in accordance with embodiments of the present disclosure. Various embodiments of the present disclosure may be used for qualitative market research, including focus group testing and interviewing; quantitative market research, including surveys; company performance assessment and human resources performance evaluations; hiring testing; clinical testing, including mental health assessment; military intelligence; product and service rating polls; political or public polling; consumer experience measurement; exit polls; consumer product testing; consumer profiling; and advertising classification by motivational impact.

In another example, the disclosed method may be used to assess the positive and negative reactions of individuals to a video or audio stimulus on a second-by-second basis, capturing these reactions and displaying them to a focus group (e.g., a "dial" or strength test). Stimuli are then reviewed alongside a visual graphic display of positive and negative reactions (like a "brain-wave readout"), enabling the group to focus on and discuss the reasons underlying the patterns in the moment-to-moment reactions.

In one example, embodiments of the present disclosure may be used to assess aspirations of one or more consumers with respect to a particular consumer product, either through interviews, surveys, testing, or a combination thereof. The results of the assessment may then be used, for example, by a manufacturer to strategically develop a marketing campaign targeting the consumer's aspirations, or to develop new products which are better at delivering on consumers' aspirations.

In another example, embodiments of the present disclosure may be used to assess emotional characteristics of one or more employees. The results of the assessment may then be used, for example, by an employer to strategically develop one or more work teams comprising employees having compatible emotional characteristics.

In another example, embodiments of the present disclosure may be used to identify the characteristics of test subjects who are interviewed, surveyed, and/or tested during market research.

In another example, embodiments of the present disclosure may be used to assess a candidate for employment during the hiring process. For example, a candidate may take a test in accordance with the present disclosure. The results of the test may then be used to choose or avoid the candidate based on the quantitative emotional profile of the candidate.

In another example, embodiments of the present disclosure may be used to screen a person for certain mental health conditions, perform diagnostic mental health testing, or develop a therapeutic treatment strategy for a patient.

In another example, embodiments of the present disclosure may be used to develop a military strategy. For example, a test in accordance with the present disclosure may be administered to a person in one place (e.g., in a country having rival factions), and the results compared with the results of similarly-tested people from another place to determine if that person is likely to harbor sentiments possessed by people in the other place (e.g., a member of the rival faction).

In another example, embodiments of the present disclosure may be used to perform product surveys on product experience, impression and reputation from an emotional point of view.

In another example, embodiments of the present disclosure may be used to survey voters after viewing or hearing a political speech or presentation to develop a political campaign strategy. For example, the campaign strategy may be developed to appeal to the motives elicited by a test conducted in accordance with one embodiment of the present disclosure.

In another example, embodiments of the present disclosure may be used to perform secret shopper testing.

In another example, embodiments of the present disclosure may be used to conduct exit polls of voters.

In another example, embodiments of the present disclosure may be used to evaluate a product against similar products, and to further design the product to meet the consumers' aspirations with respect to the similar products.

In another example, embodiments of the present disclosure may be used to perform reverse emotional engineering. For example, the results of a test conducted in accordance with one embodiment of the present disclosure may be used to develop a product that matches a consumer's aspiration to use a competing product (e.g., a high-end luxury product).

In another example, embodiments of the present disclosure may be used to classify advertisements by motivational category (i.e., instead of by topic), and then develop and present advertising having the same motivational category as those most often read by a consumer (e.g., web-based advertising).

In another example, embodiments of the present disclosure may be used to profile a prospective customer and adapt a marketing strategy based on the profile (e.g., identify the aspirations of a new car buyer to market the appropriate car to them).

In another example, embodiments of the present disclosure may be used to develop a fraud management strategy. For example, a disability insurance claimant may be profiled with respect to his attitude toward his job, and a predictive algorithm for identifying claimants who are likely to defraud insurers by not returning to their jobs when disability has diminished may be developed. Other types of fraud may be managed, including attempts by the subject to subvert the stimulus test.

In another example, embodiments of the present disclosure may be used to detect fraud or subversion of the test. For example, if the subject responds to none of the stimuli, there is no useful information for assessing the subject's emotional characteristics. Likewise the results of the test are likely to be skewed if the subject responds to the stimuli in a predictable pattern, for example by selecting every third image in the sequence or in a repeated pattern, selecting images randomly, selecting only images containing a certain color or object, or selecting all images in the set.

Other Embodiments

The hypothalamus, hippocampus, and amygdala regions of the human brain are associated with the processing of emotional reactions. Neuropsychology informs that, when stimulated, these regions of the brain react to the stimulus before the executive (e.g., cognitive) functions of the frontal lobes are activated. This reaction occurs within a period of between approximately 300 and 800 milliseconds after exposure to the stimulus. For example, it is understood that the human brain first performs recognition of a stimulus, followed by generation of an emotional response to the stimulus, which is then followed by cognitive, intellectual processing of the stimulus. According to various aspects of the present invention, it is appreciated that a subject's response to a stimulus, such as a visual stimulus, that occurs within the above time period indicates a pre-cognitive emotional reaction to the stimulus, whereas a response gained after a longer period of exposure is obtained while the subject's frontal lobes are activated, permitting the subject's response to become augmented by cognitive processing that may distort or obscure the pre-cognitive emotional reaction. Thus, a pre-cognitive emotional reaction can be elicited by limiting the amount of time the subject is exposed to the stimulus and/or limiting the amount of time the subject is permitted to respond to the stimulus.

Figure 12:
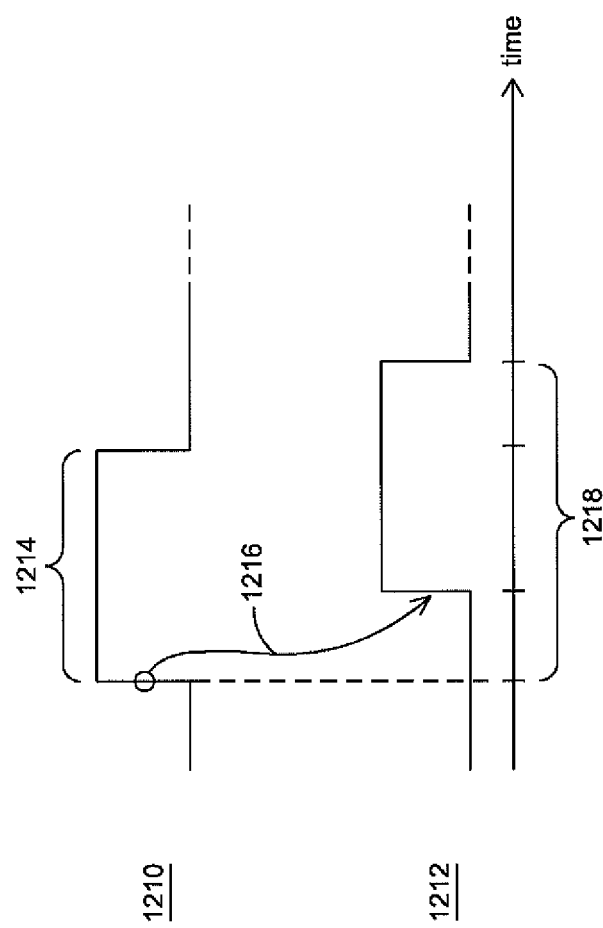
FIG. 12 illustrates an exemplary timing sequence in accordance with one embodiment of the disclosure.

FIG. 12 illustrates a timing sequence diagram according to one embodiment. Note that FIG. 12 is not drawn to scale. A stimulus exposure 1210 occurs when a subject is exposed to a stimulus for a first period of time 1214 of between approximately 500 milliseconds and approximately 1 second. The stimulus exposure 1210 may be, for example, displaying an abstract image to the subject. The stimulus is removed promptly at the end of the first period of time 1214. As discussed above, the hypothalamus, hippocampus, and amygdala regions of the subject's brain react to the stimulus before the executive functions of the frontal lobes are activated. This reaction will occur approximately 300 milliseconds to approximately 800 milliseconds after the stimulus exposure 1210 begins, as indicated by lead line 1216. A response window 1212 defines a period of time in which the subject is allowed to respond. Response window 1212 includes the first period of time 1214 (e.g., the stimulus exposure 1210 time) or within a "grace period" of up to approximately 300 milliseconds after the stimulus exposure 1210 begins, as generally indicated by reference numeral 1218. Because cognitive processing of the stimulus begins shortly after pre-cognitive processing has started, the total response time 1218 may be limited to no longer than approximately 1.3 seconds to ensure that only "pure" pre-cognitive, emotional responses are received. Responses received more than approximately 1.3 seconds after the subject has been exposed to the stimulus may be tainted by cognitive processing, and not truly reflective of the subject's emotional reaction to the stimulus.

According to an embodiment, a stimulus test may be performed using a computer. The computer includes one or more user interfaces for exposing a test subject to one or more stimuli and for receiving responses from the test subject. The computer may be configured to enforce the time limitations for exposing the stimulus and receiving the responses, such as discussed above, as well as to record the responses or other relevant data. The computer may also be configured to determine one or more motivational characteristics, or a motivational profile, of the subject based on the stimuli and corresponding responses. For example, a process for performing a stimulus test, in accordance with one embodiment, may be performed on such a computer, such as the process described below with respect to FIG. 13.

Figure 13:
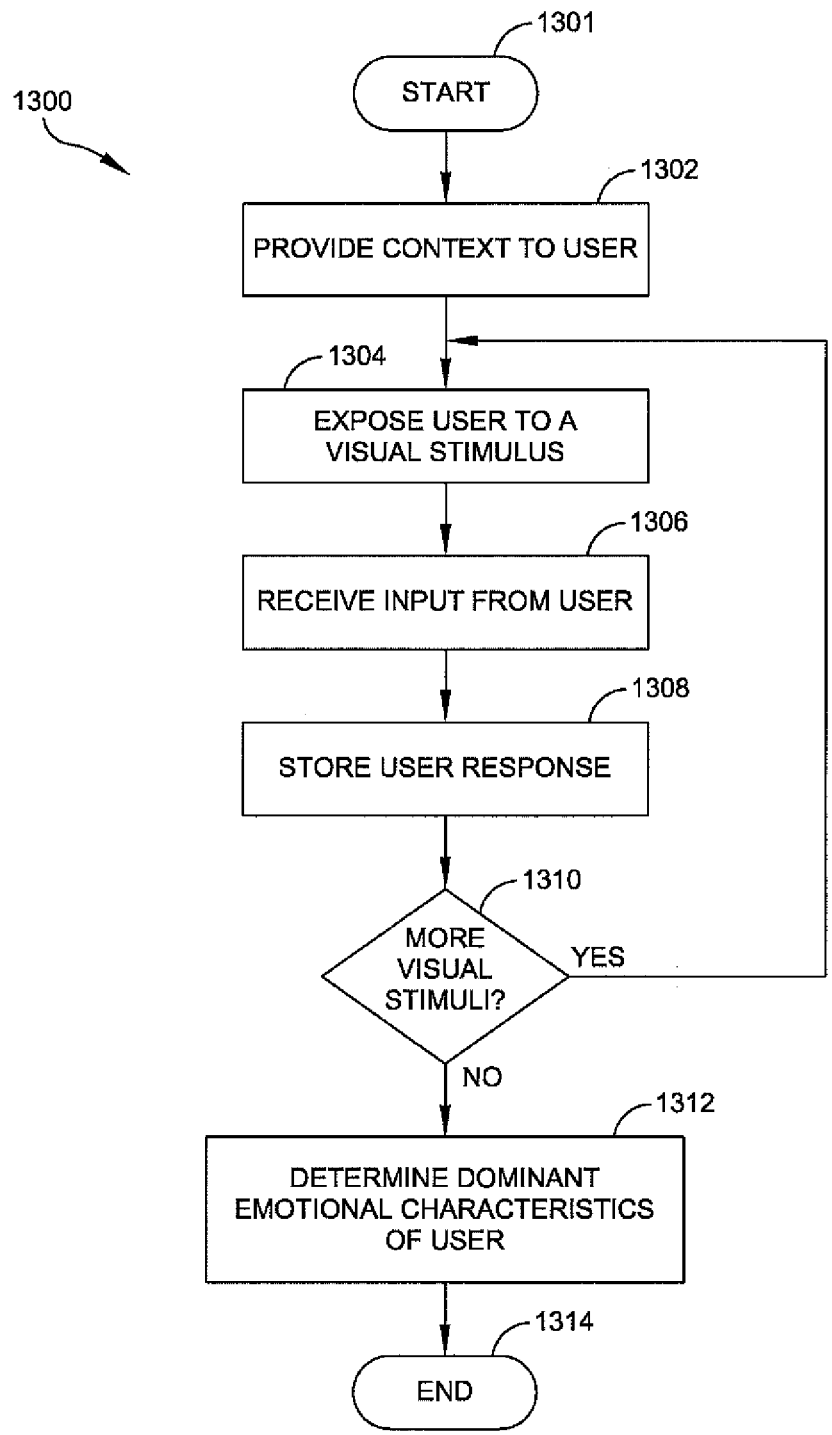
FIG. 13 illustrates an exemplary process for performing a stimulus test in accordance with one embodiment of the disclosure.

FIG. 13 illustrates a process 1300 for performing a stimulus test according to another embodiment. At block 1301, process 1300 starts. At block 1302, a user is provided with a context, such as a research topic that the user may consider while taking the stimulus test. The research topic may include a "matter at hand." The matter at hand provides a context for the test, and includes the subject matter for which the emotional state of the subject is to be elicited. The inquiry may be an incomplete sentence in the form of "Thinking about (a particular topic) makes me feel _____." For example, "Thinking about air fresheners makes me feel _____."

With the context in mind, the user is exposed to a visual stimulus at block 1304. The length of exposure may be limited to between approximately 500 milliseconds and approximately 1 second. At the end of this exposure period, the visual stimulus may be promptly removed. In this manner, the user will have enough time for simple recognition of the stimulus and the development of an emotional response to it, but not enough time for cognitive processing of the stimulus. The visual stimulus may, for example, be an abstract image drawn from a set or database of images. If the user has, for example, a positive emotional response to the visual stimulus, the user may provide an input, such as by pressing a button or using another input device. Other emotional responses, such as negative ones, may be used as a basis for causing the user to provide the input, depending on the context. The input may, for example, be a simple signal generated by the input device. At block 1306, the input, if any, is received from the user, and at block 1308, a user response is stored in response to receiving the input from the user. The user response may be any data that indicates that the user experienced an emotional reaction to the stimulus, and that also indicates what the emotional reaction was. For example, the user response may identify one of a plurality of specific emotional reactions that have previously been associated with the stimulus (e.g., through testing or another validation process). By reacting to the stimulus, it can be said that the user experienced the specific emotional reaction that is associated with the stimulus. Accordingly, it should be understood that a correlation exists between the stimulus that is presented to the user and the user's response to her exposure to the stimulus. Some stimuli may not produce a user response.

At decision block 1310, if there are additional stimuli in the set or database, process 1300 repeats at blocks 1304, 1306, and 1308 until the user has been exposed to all of the stimuli. Each stimulus may, for example, be randomly selected from the set or database of stimuli, or selected in a manner that reduces predictability of the sequence. If there are no additional stimuli, at block 1312 the dominant emotional characteristic of the user is determined based on the user response or responses. It should be understood that a variety of techniques may be employed to determine the dominant emotional characteristic of the user. For example, a tally of the user responses may be taken to determine which emotional characteristic, as identified by each user response, was indicated most often by the user during the test. In another example, the user response may include a response time, which is the amount of time that elapsed between exposing the user to the stimulus and receiving the input from the user. Accordingly, user responses with the shortest response times may indicate that the user has a stronger association with the emotional characteristic that corresponds to the stimulus than with other characteristics that the user also responded to favorably.

Process 1300 ends at block 1314.

According to another aspect, a subject is exposed to a stimulus that has been previously validated (e.g., through research, testing, or other procedures) to have a probabilistic likelihood of evoking one or more specific emotional reactions, including, for example, a stimulus known to have the power to evoke one or more specific pre-cognitive emotional reactions when the subject is exposed to the stimulus for a limited amount of time, for example, approximately 1 second or less. Non-limiting examples of such stimuli include an image of a person fastening an automotive seat belt (evokes a feeling of security), a fingerprint (identity), a surgeon performing surgery (mastery), an airplane taking off (empowerment), several business professionals working together (engagement), an athlete wearing a medal (achievement), children playing together (belonging), a mother tending to a sick child (nurturance), and a military officer being decorated with ribbons (esteem). Consequently, a pre-cognitive emotional reaction to one of the validated stimuli is indicative of the presence of the specific emotion(s) associated with the respective stimulus. Further, by limiting the response time of the subject to between approximately 300 milliseconds and 800 milliseconds, the subject's reaction is less likely to reflect intellectual processing of the stimulus that may distort or obscure the emotional reaction.

According to yet another aspect, a library of stimuli includes stimuli that are validated, for example, through research, testing, or other procedures, to evoke one or more specific emotional reactions in a subject exposed to the stimuli for a limited amount of time, for example, for approximately 1 second or less. The library may include, for example, a set of images that have been validated to evoke positive (e.g., aspirational) emotions and/or negative (e.g., frustrative) emotions. In a further embodiment, the stimuli are selected, and validated, to evoke specific emotions across cultures. For instance, stimuli that are validated to evoke a feeling of security will be known to evoke that emotion in any subject without regard to the subject's social background, religion, ethnicity, or other cultural characteristics.

According to another aspect, each stimulus in the library of validated stimuli may be liked to one or more categories in a motivational model, such as the motivational matrix 104A as described above with respect to FIGS. 1, 2, and 3. In one embodiment, these categories are organized according to a two-dimensional motivational model, wherein each category describes certain motivational characteristics. Non-limiting examples of such categories include security, empowerment, belonging, identity, engagement, nurturance, mastery, achievement, and integrity. The motivational characteristics may be, for example, quantified as degrees of aspiration, which is one manifestation of motivation. For example, one may be motivated, or aspire to, achieve some level or type of personal achievement, such as any of the exemplary characteristics described above, celebrity, wealth, respect, knowledge, power, charity, conquest, asceticism, or other forms of achievement. As shown in FIG. 2, for example, one dimension of the model quantifies the focus of aspiration as: intrapsychic (e.g., within oneself), instrumental (e.g., a mechanism for achievement), or interpersonal (e.g., relations with others). Another dimension in the example quantifies the level of aspiration as: establishing potential, optimizing process, or attaining outcomes. Accordingly, in one embodiment, each category of the motivational model may be associated with two quantifiable characteristics of aspiration (e.g., level and focus), such as shown in FIG. 2.

According to another aspect, each response by a subject to one or more stimuli may form a pattern of emotional responses that, in turn, can be interpreted using, for example, a motivational model such as described above with respect to FIGS. 1, 2, and 3, to identify one or more motivational characteristics of the subject (also referred to herein as a "motivational profile"). Such motivational characteristics may be interpreted with respect to, for example, life in general, work, interpersonal relations, personal or familial welfare, consumerism, and other motivations and aspirations. In one embodiment, the motivational characteristic may be based, for example, on an aspiration to achieve a positive result (e.g., motivated to "feel more" of something), or an aspiration to avoid a negative result (e.g., motivated to "feel less" of something). In one embodiment, a subject is provided with a stem sentence, for example, "I wish I had a job that makes me feel more _____." The stem sentence is a psychological priming act, which places the subject into a posture of psychological readiness to respond to various stimuli that are presented in an assessment test according to various aspects of the present invention. Subsequent exposure to one or more stimuli may evoke a "yes" (positive) or "no" (negative) response in relation to the topic introduced by the stem sentence. For example, if a subject completes the stem sentence as "I wish I had a job that makes me feel more expert," and who is exposed to a photograph of a man in a business suit wearing boxing gloves with one first raised high above his head, feels the emotion of success or victory, then the subject may respond "yes" to seeing the photograph (e.g., by pressing a button to indicate a "yes" response). If the photograph is associated with the motive of mastery, a subject providing a positive (e.g., "yes") response to the photograph could be said to possess the motivation of aspiring to mastery with respect to his job.

In one embodiment, a biometric measure of the strength of an emotional response elicited from a subject using one of the techniques described herein is based on the response time of the subject to each of the stimuli. For example, short response times (e.g., relative to a benchmark response time, or relative to response times for other stimuli presented during a test battery) may indicate that the subject's association with the stimulus is strong in absolute terms and/or relative to the strength of the subject's other emotional responses.

Having thus described several embodiments of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method comprising:
   maintaining a set of sensory stimuli, each of the sensory stimuli being associated with an identified reaction;
   presenting, to a subject, by a computer through a presentation interface, the sensory stimuli to the subject, including, for each sensory stimulus:
   presenting the sensory stimulus during a presentation period having a duration of more than 500 milliseconds and less than 1000 milliseconds, the duration of the presentation period having been previously defined, the duration of the presentation period being enforced by computer,
   ending the presenting of the sensory stimulus at the end of the presentation period,
   providing a grace period immediately following the end of the presentation period of time, the grace period having a duration of up to 300 milliseconds during which none of the sensory stimuli is presented, the duration of the grace period having been previously defined, the duration of the grace period being enforced by computer, and
   presenting a subsequent sensory stimulus at the end of the grace period;
   by a computer, receiving a response, by the subject, to at least one of the sensory stimuli during a response period including the presentation period and the grace period, the response of the subject to a particular sensory stimulus representing a reaction of the subject to the particular sensory stimulus in relation to a context;
   by a computer, storing information that represents the reaction of the subject to each of the sensory stimuli for which a response was received; and
   by a computer, determining, based on at least some of the stored information, an emotional characterization of the subject in relation to the context.

2. The method of claim 1, comprising identifying the context to the subject by computer through a user interface.

3. The method of claim 1, in which determining the emotional characterization of the subject is based on a time elapsed between presenting a particular sensory stimulus to the subject and receiving the response, by the subject, to the particular sensory stimulus.

4. The method of claim 1, comprising determining a motivational profile of the subject based on the emotional characterization of the subject.

5. The method of claim 1, in which determining the emotional characterization of the subject includes identifying one or more dominant emotional characteristics of the subject in relation to the context.

6. The method of claim 5, in which each of the one or more dominant emotional characteristics of the subject is associated with a motivational characteristic of a motivational model.

7. The method of claim 6, in which the motivational characteristics include one or more of security, empowerment, belonging, identity, engagement, nurturance, mastery, achievement, and esteem.

8. The method of claim 1, comprising assessing one or more of a value and a design of at least one of a product and a service with respect to the subject based on the emotional characterization of the subject.

9. The method of claim 1, comprising, based on the emotional characterization of the subject, identifying a possible association between the subject and one or more of an advertisement, a product, a service, a job, an individual, and a group of individuals.

10. The method of claim 1, in which presenting a sensory stimulus includes selecting the sensory stimulus randomly from the maintained set of sensory stimuli.

11. The method of claim 1, in which the stored information identifies the reaction that is associated with each sensory stimulus for which a response was received.

12. A non-transitory computer readable medium storing instructions for causing a computing system to:
   maintain a set of sensory stimuli, each of the sensory stimuli being associated with an identified reaction;
   present, to a subject, by a computer through a presentation interface, the sensory stimuli to the subject, including, for each sensory stimulus:
   presenting the sensory stimulus during a presentation period having a duration of more than 500 milliseconds and less than 1000 milliseconds, the duration of the presentation period having been previously defined, the duration of the presentation period being enforced by computer,
   ending the presenting of the sensory stimulus at the end of the presentation period,
   providing a grace period immediately following the end of the presentation period of time, the grace period having a duration of up to 300 milliseconds during which none of the sensory stimuli is presented, the duration of the grace period having been previously defined, the duration of the grace period being enforced by computer, and
   presenting a subsequent sensory stimulus at the end of the grace period;
   receive a response, by the subject, to at least one of the sensory stimuli during a response period including the presentation period and the grace period, the response of the subject to a particular sensory stimulus representing a reaction of the subject to the particular sensory stimulus in relation to a context;

store information that represents the reaction of the subject to each of the sensory stimuli for which a response was received; and determine, based on at least some of the stored information, an emotional characterization of the subject in relation to the context.

13. The non-transitory computer readable medium of claim 12, the instructions causing the computing system to identify the context to the subject by computer through a user interface.

14. The non-transitory computer readable medium of claim 12, in which the duration of the presentation period is sufficiently brief as to limit or prevent cognitive processing of the sensory stimulus by the subject.

15. The non-transitory computer readable medium of claim 12, in which the duration of the response period is sufficiently brief as to limit or prevent cognitive processing of the sensory stimulus by the subject.

16. The non-transitory computer readable medium of claim 12, in which determining the emotional characterization of the subject is based on a time elapsed between presenting a particular sensory stimulus to the subject and receiving the response, by the subject, to the particular sensory stimulus.

17. The non-transitory computer readable medium of claim 12, in which presenting a sensory stimulus includes selecting the sensory stimulus randomly from the maintained set of sensory stimuli.

18. A system comprising:
a processor and a memory, the processor and memory configured to:
maintain a set of sensory stimuli, each of the sensory stimuli being associated with an identified reaction;
present, to a subject, by a computer through a presentation interface, the sensory stimuli to the subject, including, for each sensory stimulus:
presenting the sensory stimulus during a presentation period having a duration of more than 500 milliseconds and less than 1000 milliseconds, the duration of the presentation period having been previously defined, the duration of the presentation period being enforced by computer,
ending the presenting of the sensory stimulus at the end of the presentation period,
providing a grace period immediately following the end of the presentation period of time, the grace period having a duration of up to 300 milliseconds during which none of the sensory stimuli is presented, the duration of the grace period having been previously defined, the duration of the grace period being enforced by computer, and
presenting a subsequent sensory stimulus at the end of the grace period;
receive a response, by the subject, to at least one of the sensory stimuli during a response period including the presentation period and the grace period, the response of the subject to a particular sensory stimulus representing a reaction of the subject to the particular sensory stimulus in relation to a context;
store information that represents the reaction of the subject to each of the sensory stimuli for which a response was received; and
determine, based on at least some of the stored information, an emotional characterization of the subject in relation to the context.

* * * * *